(12) United States Patent
Lee et al.

(10) Patent No.: US 11,730,449 B2
(45) Date of Patent: *Aug. 22, 2023

(54) ULTRASONIC DIAGNOSTIC SYSTEM

(71) Applicant: SAMSUNG MEDISON CO., LTD., Gangwon-do (KR)

(72) Inventors: Yunju Lee, Seongnam-si (KR); Gilju Jin, Seongnam-si (KR); Mijeoung Ahn, Seongnam-si (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 1080 days.

This patent is subject to a terminal disclaimer.

(21) Appl. No.: 16/195,380

(22) Filed: Nov. 19, 2018

(65) Prior Publication Data

US 2019/0090846 A1  Mar. 28, 2019

Related U.S. Application Data

(63) Continuation-in-part of application No. 14/326,395, filed on Jul. 8, 2014, now Pat. No. 10,130,335, which
(Continued)

(30) Foreign Application Priority Data

Apr. 12, 2011 (KR) .................. 10-2011-0033955
Sep. 22, 2011 (KR) .................. 10-2011-0095916

(51) Int. Cl.
*A61B 8/00* (2006.01)
*A61B 8/08* (2006.01)
*A61B 8/14* (2006.01)

(52) U.S. Cl.
CPC .......... *A61B 8/4427* (2013.01); *A61B 8/4405* (2013.01); *A61B 8/4433* (2013.01);
(Continued)

(58) Field of Classification Search
CPC ... A61B 8/4427; A61B 8/4405; A61B 8/4433; A61B 8/145; A61B 8/5207; A61B 8/565
See application file for complete search history.

(56) References Cited

U.S. PATENT DOCUMENTS 5,882,310 A   3/1999  Marian, Jr.
5,893,363 A   4/1999  Little et al.
(Continued)

FOREIGN PATENT DOCUMENTS

EP    2105094 A8    12/2009
JP    2006-519684 A    8/2006
(Continued)

OTHER PUBLICATIONS

European Search Report issued in European Patent Application No. 12163975.1 dated Jun. 18, 2012.
(Continued)

*Primary Examiner* — Boniface Ngathi N
*Assistant Examiner* — Zainab Mohammed Aldarraji
(74) *Attorney, Agent, or Firm* — Morgan, Lewis & Bockius LLP

(57) ABSTRACT

An ultrasound diagnostic system includes a portable ultrasound diagnostic device and an extended docking device to which the portable ultrasound diagnostic device is detachably mounted, wherein at least one of the probes and channels are extended when the portable ultrasound diagnostic device is mounted to the extended docking device. Also, the ultrasound diagnostic system may further include an indoor ultrasound diagnostic device including a portable docking part, and the portable ultrasound diagnostic device may include a cart-based docking part and be connected to the indoor ultrasound diagnostic device. The ultrasound diagnostic system may enhance portability of the portable ultrasound diagnostic device and simultaneously achieves
(Continued)

superior ultrasound diagnostic performance and quality also in the portable ultrasound diagnostic device through extension of the probes, signal channels, diagnostic items, or diagnostic performance, as occasion demands.

11 Claims, 15 Drawing Sheets

Related U.S. Application Data is a continuation-in-part of application No. 13/445,470, filed on Apr. 12, 2012, now abandoned.

(52) U.S. Cl.
CPC ............ *A61B 8/145* (2013.01); *A61B 8/5207* (2013.01); *A61B 8/565* (2013.01)

(56) References Cited

U.S. PATENT DOCUMENTS

| | | | |
|---|---|---|---|
| 6,447,451 | B1 | 9/2002 | Wing et al. |
| 7,352,570 | B2 | 4/2008 | Smith et al. |
| 2003/0097071 | A1 | 5/2003 | Halmann et al. |
| 2004/0150963 | A1 | 8/2004 | Holmberg et al. |
| 2004/0179332 | A1* | 9/2004 | Smith .................... A61B 50/13 361/679.41 |
| 2008/0055826 | A1* | 3/2008 | Smith .................... A61B 90/36 361/679.23 |
| 2008/0146922 | A1* | 6/2008 | Steins .................... A61B 8/546 600/437 |
| 2008/0161688 | A1* | 7/2008 | Poland ................ G01S 7/52084 600/437 |
| 2009/0275835 | A1 | 11/2009 | Hwang et al. |

FOREIGN PATENT DOCUMENTS

| | | |
|---|---|---|
| JP | 2009-240436 A | 10/2009 |
| KR | 10-1998-081072 A | 11/1998 |
| KR | 10-2010-0054978 A | 5/2010 |
| WO | 2006/111873 A3 | 3/2007 |

OTHER PUBLICATIONS

Korean Office Action, w/ English translation thereof, issued in Korean Patent Application No. KR 10-2011-0095916 dated Aug. 1, 2013.

United States Office Action issued in U.S. Appl. No. 13/445,470 dated Apr. 8, 2014.

United States Office Action issued in U.S. Appl. No. 13/445,470 dated Dec. 30, 2013.

United States Office Action issued in U.S. Appl. No. 13/445,470 dated Jun. 14, 2013.

United States Notice of Allowance dated Jul. 13, 2018 issued in U.S. Appl. No. 14/326,395.

United States Office Action dated Jun. 26, 2017 issued in U.S. Appl. No. 14/326,395.

\* cited by examiner

ULTRASONIC DIAGNOSTIC SYSTEM

CROSS-REFERENCE TO RELATED APPLICATION

This application is a Continuation-In-Part of U.S. patent application Ser. No. 14/326,395, filed on Jul. 8, 2014, which is a Continuation-In-Part of U.S. patent application Ser. No. 13/445,470, filed on Apr. 12, 2012, which claims the benefit of Korean Patent Application Nos. P2011-0033955, Filed on Apr. 12, 2011 and P2011-0095916, filed on Sep. 22, 2011, the disclosures of which are incorporated herein by reference.

BACKGROUND

1. Field

The present subject matter relates to an ultrasound diagnostic system capable of enhancing portability of a portable ultrasound diagnostic device and simultaneously superior ultrasound diagnostic performance and quality of the portable ultrasound diagnostic device through extension of probes and/or signal channels as occasion demands.

2. Description of the Related Art

Ultrasound diagnostic systems have noninvasive and non-destructive characteristics. Ultrasound diagnostic systems provide medical doctors with high resolution images of inner tissues of objects, without a need for surgical operations to directly incise the objects to observe the objects. The noninvasiveness and high resolution images of the ultrasound diagnostic systems promote wide use of the ultrasound diagnostic systems in the field of medicine to obtain information on objects within a human body.

Such ultrasound diagnostic systems, however, are very large and heavy, so need to be fixed to particular places. Since even small size ultrasound diagnostic systems are 10 kg or more in weight, they are not easy to carry. Meanwhile, since ultrasound diagnostic systems are used in emergency rooms, operation rooms, or any other places, where the ultrasound diagnostic systems must frequently be moved, the ultrasound diagnostic systems need to be small. Needs for small size ultrasound diagnostic devices encourage development of portable ultrasound diagnostic devices.

FIG. 1 is a view schematically illustrating a portable ultrasound diagnostic device according to the related art. As shown in FIG. 1, one probe 101 is generally mounted at the conventional portable ultrasound diagnostic device 100 for portability, and the portable ultrasound diagnostic device 100 has a limited number of signal channels corresponding to the probe 101. Although the conventional portable ultrasound diagnostic device 100 is suitable to promote convenience of portability or movement, there is an extreme limit as to the number of probes to be mounted at the same. Consequently, since only a particular sort of probe may be mounted at the conventional portable ultrasound diagnostic device 100 due to limitations on number of probes mounted on the ultrasound diagnostic device 100, the conventional ultrasound diagnostic device is used for limited purposes of particular diagnosis.

In addition, the conventional portable ultrasound diagnostic device has a limit as to the number of signal channels to be provided for the sake of portability, which thereby deteriorates resolution and quality of produced ultrasound images.

Furthermore, since portable ultrasound diagnostic devices have many limitations in terms of size, weight, power consumption, and the like, the portable ultrasound diagnostic devices show poor ultrasound diagnostic performance and quality compared with cart-based ultrasound diagnostic devices.

SUMMARY

An aspect of the present invention encompasses an ultrasound diagnostic system capable of enhancing portability of a portable ultrasound diagnostic device and achieving superior ultrasound diagnostic performance and quality through extension of probes and/or signal channels as occasion demands.

Another aspect of the present invention relates to an ultrasound diagnostic system. The ultrasound diagnostic system includes a probe that includes a plurality of transducer elements; a portable ultrasound diagnostic device that includes a first channel board for performing beamforming of at least one of signals transmitted or received to or from the plurality of transducer elements; and a docking device on which the portable ultrasound diagnostic device is detachably mounted, and that includes a second channel board for performing beamforming of at least one of the signals transmitted or received to or from the plurality of transducer elements.

The first channel board may perform beamforming by using a less number of channels than number of the transducer elements.

The second channel board may perform beamforming by using channels equal to number of the transducer elements.

The second channel board may perform beamforming of signals equal to number of signals transmitted or received to or from the probe.

The second channel board may perform beamforming of signals, for which beamforming is not performed by the first channel board, among the signals transmitted or received to or from the plurality of transducer elements.

Number of channels, for which beamforming is performed by the second channel board, may be greater than number of channels for which beamforming is performed by the first channel board.

The probe may transmit a plurality of ultrasound echo signals respectively corresponding to the plurality of transducer elements, the first channel board may receive and collect some of the plurality of ultrasound echo signals transmitted from the probe, and the second channel board may receive at least one ultrasound echo signal, corresponding to at least one channel, of the plurality of ultrasound echo signals transmitted from the probe, and collect the received at least one ultrasound echo signal.

The portable ultrasound diagnostic device may include an image processing unit that receives at least one ultrasound echo signal received and collected by the second channel board, and generates an ultrasound image by using the received at least one ultrasound echo signal and a more number of ultrasound echo signals than number of ultrasound echo signals received and collected by the portable ultrasound diagnostic device.

The image processing unit may generate the ultrasound image by using at least one selected from the ultrasound echo signals received and collected by the first channel board and the at least one ultrasound echo signal transmitted from the second channel board.

The docking device may pre-process the at least one ultrasound echo signal, received and collected by the second channel board, of a plurality of ultrasound echo signals respectively acquired from the plurality of transducer elements, and transmit the pre-processed ultrasound echo signal to the portable ultrasound diagnostic device.

The portable ultrasound diagnostic device may include a probe selective assembly (PSA) that respectively receives K number of ultrasound echo signals from K number of transducer elements, and parallelly transmits N number of ultrasound echo signals among the K ultrasound echo signals respectively received from the K transducer elements and signals other than the N ultrasound echo signals among the K ultrasound echo signals.

The N may vary according to a kind of the probe.

The second channel board may include at least one channel board unit that performs a reception beamforming operation and a transmission beamforming operation on at least one signal, and the at least one channel board unit may include: a transmission unit that performs the transmission beamforming operation to supply a pulse for driving the plurality of transducer elements; and a reception unit that performs the reception beamforming operation to receive and collect ultrasound echo signals from the plurality of transducer elements.

The first channel board may include at least one channel board unit that performs a reception beamforming operation and a transmission beamforming operation on at least one signal, and the at least one channel board unit may include: a transmission unit that performs the transmission beamforming operation to supply a pulse for driving the plurality of transducer elements; and a reception unit that performs the reception beamforming operation to receive and collect ultrasound echo signals from the plurality of transducer elements.

The first channel board may receive and collect M number of ultrasound echo signals among N number of ultrasound echo signals transmitted from the probe, and generate pieces of ultrasound data respectively corresponding to M number of channels, the second channel board may receive and collect signals other than the M ultrasound echo signals among the N ultrasound echo signals, and generate pieces of ultrasound data respectively corresponding to N-M number of channels, and the image processing unit may generate an ultrasound image by scan-converting the pieces of ultrasound data generated by the first channel board and the pieces of ultrasound data generated by the second channel board.

The second channel board may receive and collect N number of ultrasound echo signals transmitted from the probe, and generate pieces of ultrasound data respectively corresponding to N number of channels, and the image processing unit may generate an ultrasound image by scan-converting the pieces of ultrasound data which are generated by the second channel board and respectively correspond to the N channels.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
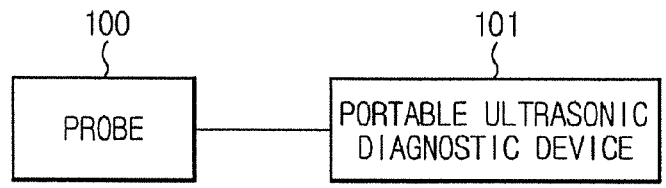
FIG. 1 is a view schematically illustrating a portable ultrasound diagnostic device according to the related art.

Reference will now be made in detail to the embodiments of the present invention, examples of which are illustrated in the accompanying drawings, wherein like reference numerals refer to like elements throughout.

Embodiments of the present invention will be described in detail to be easily embodied by those of ordinary skill in the art with reference to the accompanying drawings. The present invention may, however, be embodied in many different forms and should not be construed as being limited to the embodiments set forth herein. In the accompanying drawings, a portion irrelevant to a description of the present invention will be omitted for clarity. Moreover, like reference numerals refer to like elements throughout.

In this disclosure below, when one part (or element, device, etc.) is referred to as being 'connected' to another part (or element, device, etc.), it should be understood that the former may be 'directly connected' to the latter, or 'electrically connected' to the latter via an intervening part (or element, device, etc.). Furthermore, when it is described that one comprises (or includes or has) some elements, it should be understood that it may comprise (or include or has) only those elements, or it may comprise (or include or have) other elements as well as those elements if there is no specific limitation. Moreover, each of terms such as " . . . unit", " . . . device" and "module" described in specification denotes an element for performing at least one function or operation, and may be implemented in hardware, software or the combination of hardware and software.

The term "ultrasound image" used herein denotes an image of an object acquired by using an ultrasound wave. Also, the term "object" used herein may include a person, an animal, a part of the person, or a part of the animal. For example, an object may include an organ such as a liver, a heart, a womb, a brain, breasts, an abdomen, or the like, or a blood vessel. Also, the term "object" may include a phantom. The phantom denotes a material having a volume that is very close to a density and effective atomic number of an organism, and may include a spherical phantom having a characteristic similar to a physical body.

Moreover, the term "user" used herein is a medical expert, and may be a doctor, a nurse, a medical technologist, a medical image expert, or the like, or may be an engineer repairing a medical apparatus. However, the user is not limited thereto.

Figure 2:
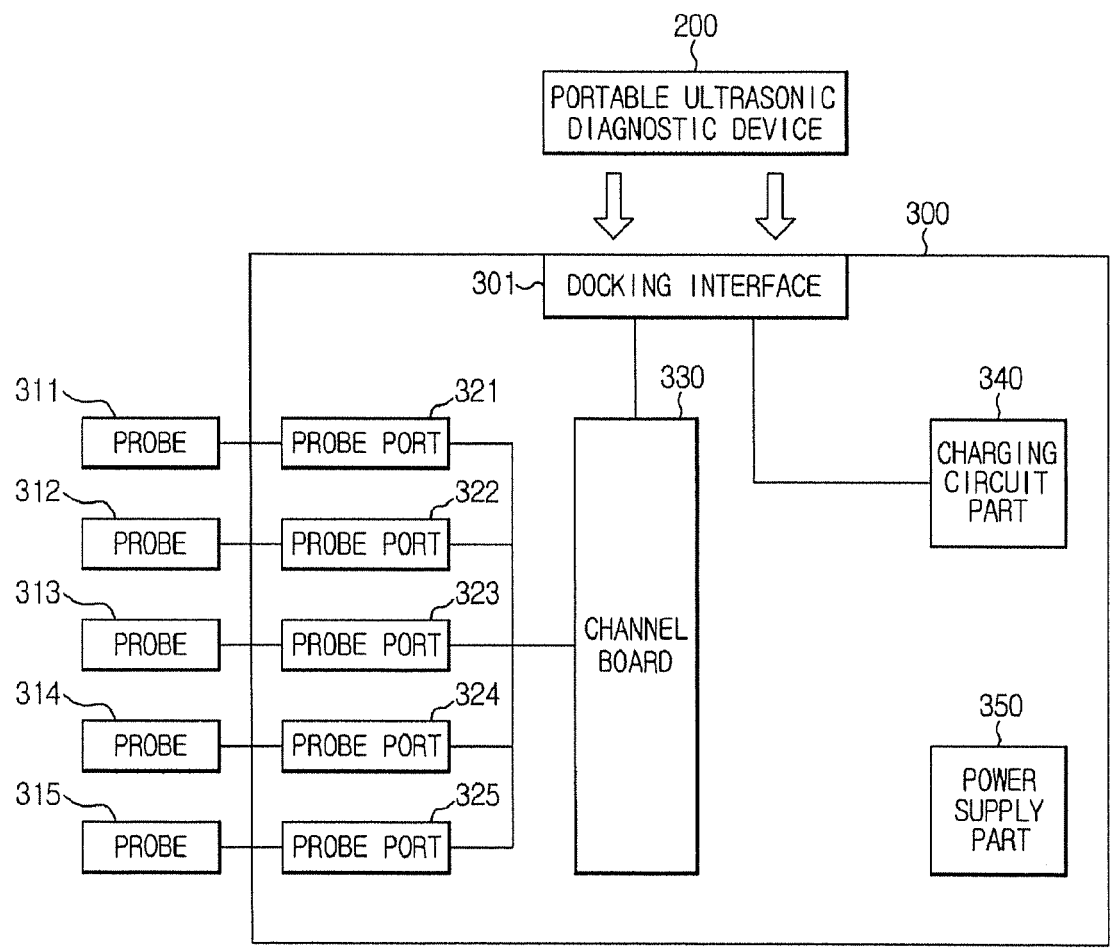
FIG. 2 is a control block diagram illustrating an ultrasound diagnostic system according to a first embodiment of the present invention.

FIG. 2 is a control block diagram illustrating an ultrasound diagnostic system according to the first embodiment.

As shown in FIG. 2, the ultrasound diagnostic system according to the first embodiment includes a portable ultrasound diagnostic device 200 and an extended docking device 300 to detachably mount the portable ultrasound diagnostic device 200. In this case, the portable ultrasound diagnostic device 200 may be formed integrally with a probe (not shown) including a plurality of transducer elements, and may be implemented in a portable form. In detail, the portable ultrasound diagnostic device 200 refers to a device that is connected via a wire or wirelessly to the extended docking device 300 and provides a user with an ultrasound image by using received ultrasound image data. A detailed configuration in which the portable ultrasound diagnostic device 200 is connected to the extended docking device 300 integrated with the probe will be described in more detail below with reference to FIG. 3B.

The extended docking device 300 may include a docking interface 301 for connection with the portable ultrasound diagnostic device 200, at least one probe port including probe ports 321 to 325 to respectively receive probes 311 to 315, a channel board 330 capable of extending signal channels corresponding to the probe ports 321 to 325, and a charging circuit part 340 to charge a secondary battery (not shown) during mounting of the portable ultrasound diagnostic device 200.

Figure 3A:
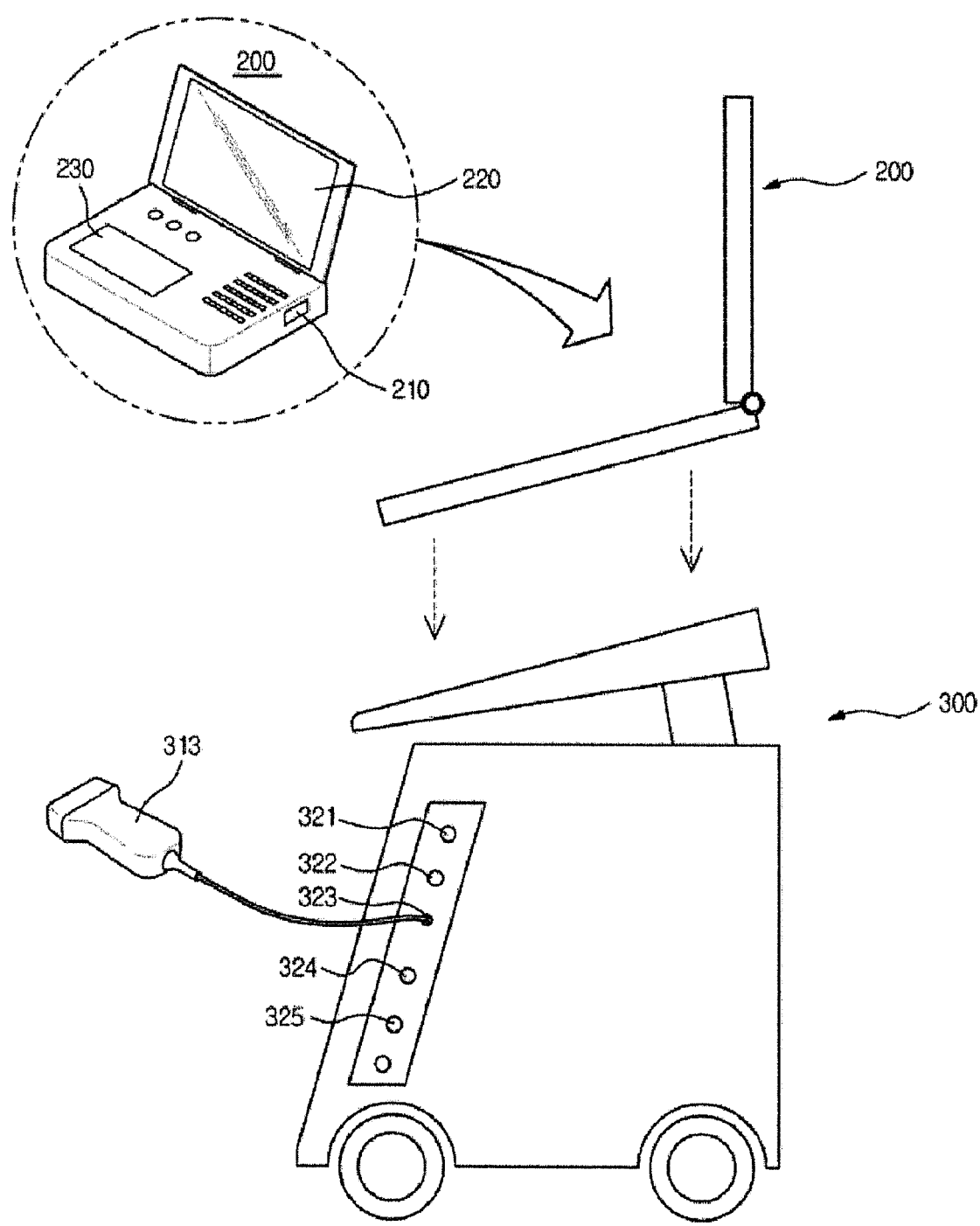
FIGS. 3A through 3C are side views of portable ultrasound diagnostic devices according to embodiments.

FIG. 3A is a side view illustrating the portable ultrasound diagnostic device 200 and the extended docking device 300 mounting the same according to the first embodiment.

Referring to FIG. 3A, in the case of requiring portability of the ultrasound diagnostic device for outdoor diagnosis, ultrasound diagnosis may be easily executed using only the portable ultrasound diagnostic device 200 including a display part 220, an input part 230, and a probe port 210. On the other hand, in the case of requiring high quality images or additional probe ports besides the probe port 210 included in the portable ultrasound diagnostic device 200, the portable ultrasound diagnostic device 200 may be mounted at the extended docking device 300.

Figure 3B:
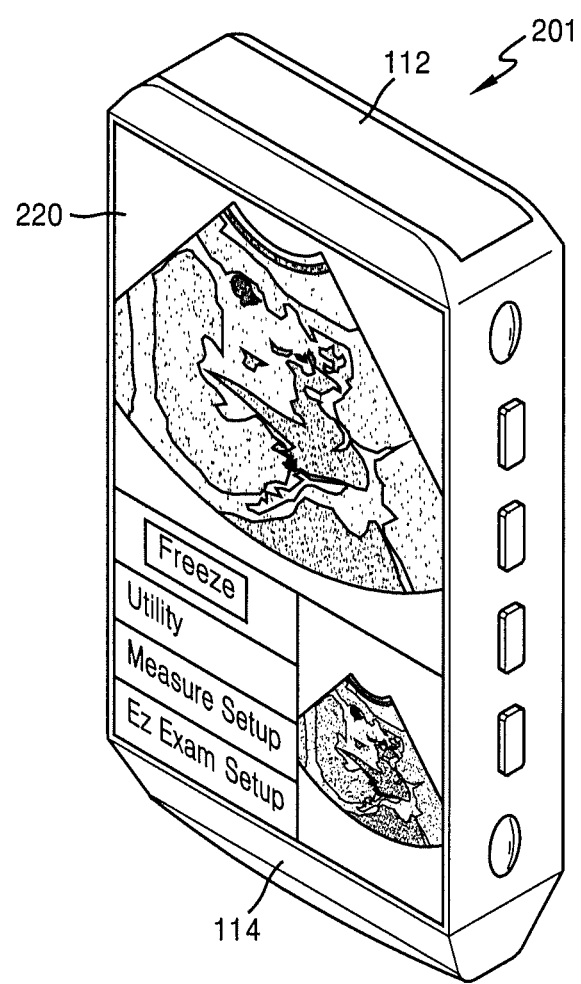

FIG. 3B illustrates a portable ultrasound diagnostic device 201 according to another embodiment. The portable ultrasound diagnostic device 201 may be easy to carry like the portable ultrasound diagnostic device 200 of FIG. 3A and may correspond to the portable ultrasound diagnostic device 200.

Furthermore, in the following drawings including FIGS. 3A and 3B, like reference numerals denote like elements.

Referring to FIG. 3B, the portable ultrasound diagnostic device 201 may be an integrated ultrasound diagnostic device including probes 112 and 114. According to an embodiment, the portable ultrasound diagnostic device 201 may include at least one probe 112 and 114 and a display part 220.

Although FIG. 3B shows that the portable ultrasound diagnostic device 201 includes the two probes 112 and 114, embodiments are not limited thereto.

The portable ultrasound diagnostic device 201 transmits ultrasound signals to an object via the probes 112 and 114 and analyzes echo signals reflected from the object to acquire ultrasound data. The number of transducer elements included in the probes 112 and 114 may be different from each other. Furthermore, the probes 112 and 114 may have different specifications, and for example, arrangement of transducer elements, a frequency of an ultrasound signal, etc. may differ for each of the probes 112 and 114. In detail, the portable ultrasound diagnostic device 201 may generate an ultrasound image based on ultrasound data and display the generated ultrasound image on the display part 220.

In addition, the portable ultrasound diagnostic device 201 may control at least one of the ultrasound data and the ultrasound image based on a user input.

Figure 3C:
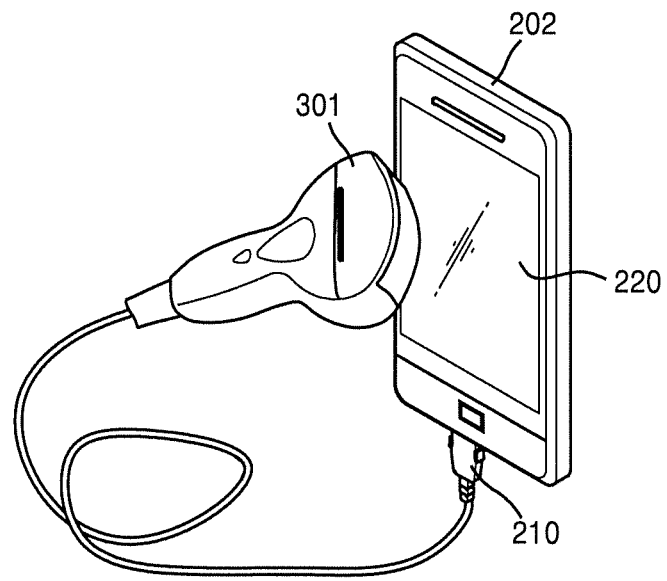

FIG. 3C illustrates a portable ultrasound diagnostic device 202 according to another embodiment. The portable ultrasound diagnostic device 202 of FIG. 3C may be easy to carry like the portable ultrasound diagnostic device 200 of FIG. 3A and may correspond to the portable ultrasound diagnostic device 200. Referring to FIG. 3C, the portable ultrasound diagnostic device 202 includes a display part 220 and a probe port 210 and may be coupled to a probe 301 via the probe port 210. The portable ultrasound diagnostic device 202 may generate an ultrasound image based on ultrasound data corresponding to ultrasound signals received by the probe 301 and display the generated ultrasound image on the display part 220.

Furthermore, the portable ultrasound diagnostic device 202 may control at least one of the ultrasound data and the ultrasound image based on a user input.

Hereinafter, operation of the ultrasound diagnostic system according to the exemplary embodiment of the present invention will be described in detail with reference to FIGS. 2 through 3C.

The ultrasound diagnostic system of the exemplary embodiment has a structure in which each of the portable ultrasound diagnostic devices 200, 201, and 202 may be coupled to the extended docking device 300 capable of extending the probes and/or signal channels. That is, the ultrasound diagnostic system of the first embodiment is provided with the extended docking device 300 at a lower part of the system, to which each of the portable ultrasound diagnostic devices 200, 201, and 202 is coupled or docked, as shown in FIGS. 2 through 3C. In accordance with such a structure, the extension of the probes and/or signal channels may be achieved during docking of the two devices, and the specific description thereof is as follows. Hereinafter, the portable ultrasound diagnostic device 200 of FIG. 3A will be described and shown as an example of the portable ultrasound diagnostic devices 200, 201, and 202 which are capable of being connected to the extended docking device 300.

First, the portable ultrasound diagnostic device 200 may be detachably mounted at the extended docking device 300 through the docking interface 301, as shown in FIG. 2. In this case, an array pin type connector (not shown) may be used for coupling or mounting the portable ultrasound diagnostic device 200 to the extended docking device 300. Since the portable ultrasound diagnostic device 200 may be easily attached to or detached from the extended docking device 300, ultrasound diagnosis may be easily performed by detaching the portable ultrasound diagnostic device 200 from the extended docking device 300, in case of requiring simple portability while not requiring ultrasound images of high quality in the ultrasound diagnostic device.

Furthermore, the portable ultrasound diagnostic device 200 may be coupled through the docking interface 310 to the extended docking device 300 via a wireless or wired communication network.

Alternatively, in case of requiring a certain level of portability while requiring ultrasound images of high quality or performance in the ultrasound diagnostic device, ultrasound diagnosis may be achieved by mounting or coupling the portable ultrasound diagnostic device 200 to the extended docking device 300. That is, the extended docking device 300 includes a plurality of probe ports 321 to 325 which receive a plurality of probes 311 to 315 respectively, as shown in FIGS. 2 and 3. Here, various types of probes may be applied as the plural probes 311 to 315 depending on diagnostic purposes. For example, the various types of probes, such as a linear probe for carotid diagnosis, a convex probe for abdominal diagnosis, a phased array probe for heart diagnosis, and the like, may be applied. Accordingly, a range of a usable probe may extend through the plural probe ports 321 to 325 included in the extended docking device 300. The number of the probe ports are not limited to five, and any number of probe ports may be provided.

The extended docking device 300 includes the channel board 330 having the signal channels corresponding to the probe ports 321 to 325, and usable channels may increase in the portable ultrasound diagnostic device 200 through the signal channels included in the channel board 330. The number of signal channels included in the channel board 330 may increase according to desired resolution and quality of the ultrasound images.

As such, when the portable ultrasound diagnostic device 200 is mounted to the extended docking device 300, at least one of probes and channels may be extended through the plural probe ports 321 to 325 and/or the channel board 330.

Furthermore, when the portable ultrasound diagnostic device 201 or 202 described with reference to FIG. 3B or 3C is connected to the extended docking device 300, by using the channel board 330 in the extended docking device 300, it is possible to increase the number of signal channels that are to be processed by the portable ultrasound diagnostic device 201 or 202 in accordance with the number of channels corresponding to transducer elements in a probe (e.g., the probe 112, 114, or 301) connected to the portable ultrasound diagnostic device 201 or 202.

In order to achieve the extension of the probes and/or the extension of the number of the signal channels, the portable ultrasound diagnostic device 200 should receive software of the extended docking device 300, for maintaining compatibility between the portable ultrasound diagnostic device 200 and the extended docking device 300.

Meanwhile, the portable ultrasound diagnostic device 200 may include the secondary battery (not shown) as a power supply unit, and the extended docking device 300 may include the charging circuit part 340 to charge the secondary battery during mounting of the portable ultrasound diagnostic device 200. That is, the portable ultrasound diagnostic device 200 has the secondary battery (not shown) used as the power supply unit for portability. When the portable ultrasound diagnostic device 200 is mounted to the extended docking device 300, the secondary battery is automatically charged through the charging circuit part 340.

Figure 4:
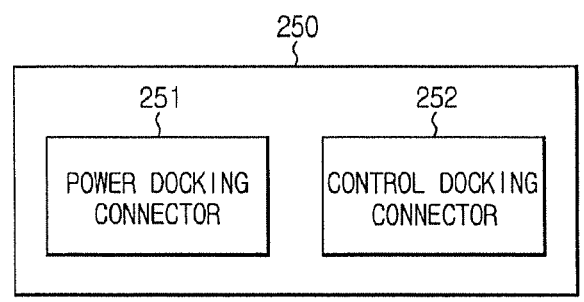
FIG. 4 is a control block diagram illustrating an extended docking part of a portable ultrasound diagnostic device in the ultrasound diagnostic system of the first embodiment.

Although not specifically described in the illustrated embodiment, the extended docking device 300 may include a hardware element for the channel extension, a circuit for generation and control of a variety of pulses, a power supply hardware element including a power supply part 350, a heat generating unit, etc. FIG. 4 is a control block diagram illustrating docking connectors of the portable ultrasound diagnostic device in the ultrasound diagnostic system according to the exemplary embodiment.

In the ultrasound diagnostic system according to the exemplary embodiment, the array pin type connector (not shown) may be used for coupling or mounting the portable ultrasound diagnostic device 200 as the upper device to the extended docking device 300 as the lower device, as described above. As shown in FIG. 4, the portable ultrasound diagnostic device 200 may include an extended docking part 250 to dock the extended docking device 300, and the extended docking part 250 may include a power docking connector 251 to couple a power between the portable ultrasound diagnostic device 200 and the extended docking device 300, and a control docking connector 252 to control operations between the portable ultrasound diagnostic device 200 and the extended docking device 300.

When the power docking connector 251 is separated from the control docking connector 252 as described above, power docking and control docking may be separately performed, thereby removing noise generated when one connector is used. As a result, it is possible to prevent performance deterioration of the ultrasound diagnostic device.

There is a case where a portable ultrasound diagnostic device is used independently. Alternatively, there is another case where a portable ultrasound diagnostic device is used with being mounted to the extended docking device 300 as described above, to perform outdoor diagnosis. Then, a diagnostic result obtained from the portable ultrasound diagnostic device is analyzed as a more vivid image. An additional function, which is absent from the portable ultrasound diagnostic device, is further performed on the diagnostic result inside a room.

Accordingly, a portable ultrasound diagnostic device 400 of an ultrasound diagnostic system according to another exemplary embodiment may further include a cart-based docking part 480 connected to an indoor ultrasound diagnostic device 500. The ultrasound diagnostic system may further include the indoor ultrasound diagnostic device 500 having a portable docking part 580 connected to the portable ultrasound diagnostic device 400. In this case, the portable ultrasound diagnostic device 400 may correspond to the portable ultrasound diagnostic devices 200, 201, or 202 described with reference to FIGS. 2 through 3C.

Figure 5A:
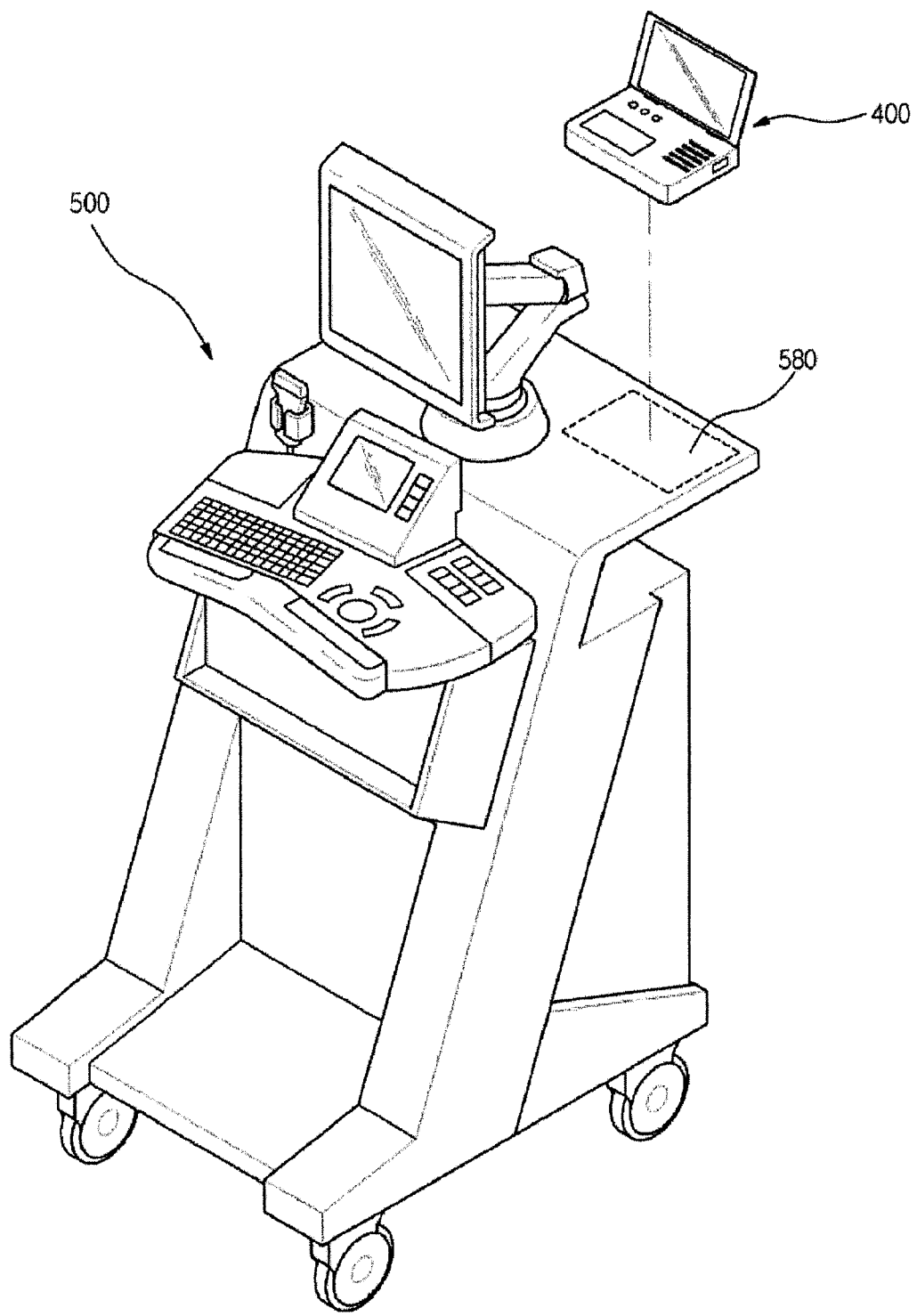
FIGS. 5A through 5C are external perspective views of ultrasound diagnostic systems according to other embodiments.

FIG. 5A is a perspective view illustrating an entire configuration of the ultrasound diagnostic system according to the second embodiment.

As shown in FIG. 5A, the ultrasound diagnostic device used indoors or the indoor ultrasound diagnostic device 500 is an ultrasound diagnostic device, which is generally used for ultrasound diagnosis and is not portable. Such an indoor ultrasound diagnostic device 500 is often referred to as a cart-based device. The ultrasound diagnostic device 500 need not necessarily be used indoors, but is referred to as an indoor ultrasound diagnostic device for convenience. Since all components in the illustrated embodiment are similar to components of a general ultrasound diagnostic device, except for the portable docking part 580 of the indoor ultrasound diagnostic device 500 utilized in the exemplary embodiments, no description thereof will be given in detail.

The indoor ultrasound diagnostic device 500 has little limit in terms of size, weight, power consumption, and the like, compared with the portable ultrasound diagnostic device 400. Thus, the indoor ultrasound diagnostic device 500 may be developed as a high performance device having various diagnostic items. When the portable ultrasound diagnostic device 400 is mounted to the indoor ultrasound diagnostic device 500, the portable ultrasound diagnostic device 400 may produce a high performance. Here, a position at which the portable ultrasound diagnostic device 400 is mounted to the indoor ultrasound diagnostic device 500 is not limited to that shown in FIG. 5A. The portable ultrasound diagnostic device 400 may be located at any position of the indoor ultrasound diagnostic device as a user may simultaneously and easily utilize the portable ultrasound diagnostic device 400 and the indoor ultrasound diagnostic device 500.

Furthermore, when the portable ultrasound diagnostic device 400 corresponds to the portable ultrasound diagnostic device 201 or 202 described with reference to FIG. 3B or 3C, the portable ultrasound diagnostic device 400 may be connected to the indoor ultrasound diagnostic device 500 via a wire or wirelessly.

For example, the portable ultrasound diagnostic device 400 may correspond to the portable ultrasound diagnostic device 201 of FIG. 3B, and may be formed integrally with a probe (not shown) including a plurality of transducer elements. In detail, the portable ultrasound diagnostic device 400 refers to a device that is connected to the indoor ultrasound diagnostic device 500 by using a wireless or wired communication method (including universal serial bus (USB)) and provides a user with an ultrasound image by using received ultrasound image data. For example, the portable ultrasound diagnostic device 400 may be a smart device that is used by downloading and installing an app (application) on a smartphone or the like.

In detail, the portable ultrasound diagnostic device 400 is a device that is connected to the indoor ultrasound diagnostic device 500 by using a wired or wireless communication method and provides the user with an ultrasound image by using received ultrasound image data.

For example, the wireless communication method may include at least one from among short-range data communication methods including a 60 GHz millimeter wave (mmWave) Wireless Local Area Network (WLAN), Wireless Fidelity (Wi-Fi), Bluetooth, Zigbee, Wi-Fi Direct (WFD), Infrared Data Association (IrDA), Bluetooth Low Energy (BLE), Near Field Communication (NFC), Wireless Broadband Internet (WiBro), World Interoperability for Microwave Access (WiMAX), Shared Wireless Access Protocol (SWAP), Wireless Gigabit Alliance (WiGig), and radio frequency (RF) communication.

Figure 5B:
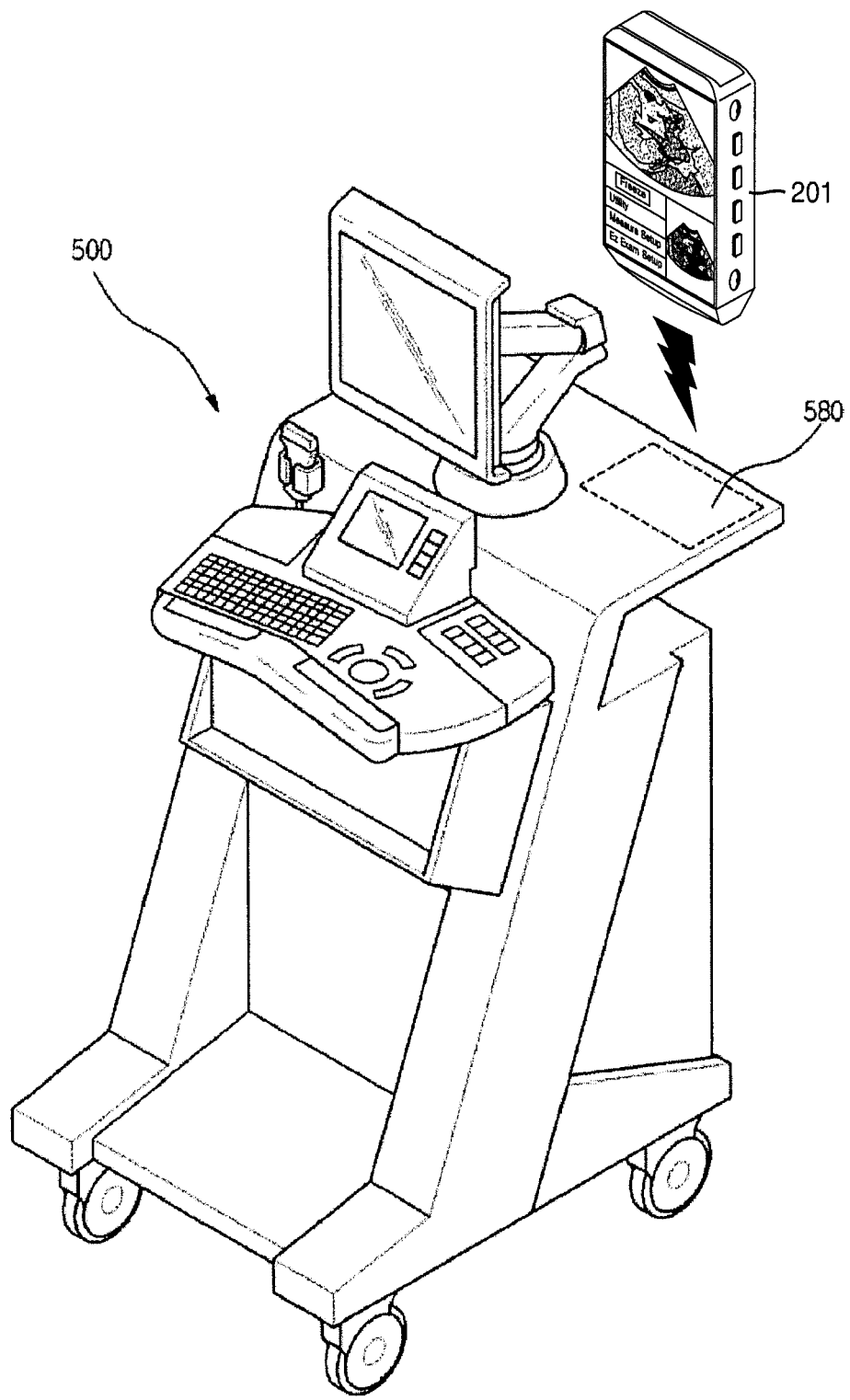

FIG. 5B illustrates an ultrasound diagnostic system in which the portable ultrasound diagnostic device 201 of FIG. 3B is connected to a cart-based ultrasound diagnostic device 500.

The cart-based ultrasound diagnostic device 500 may be connected to the portable ultrasound diagnostic device 201 by using the above-described wireless communication methods. In detail, the portable ultrasound diagnostic device 201 may have at least one wireless communication module (not shown) therein for performing at least one of the above-described wireless communication methods. Furthermore, the portable docking part 580 of the cart-based ultrasound diagnostic device 500 may include at least one wireless communication module (not shown) for performing wireless communication with the portable ultrasound diagnostic device 201. In this case, the wireless communication module in the cart-based ultrasound diagnostic device 500 may be a module for performing communication according to at least one of the above-described wireless communication methods.

Figure 5C:
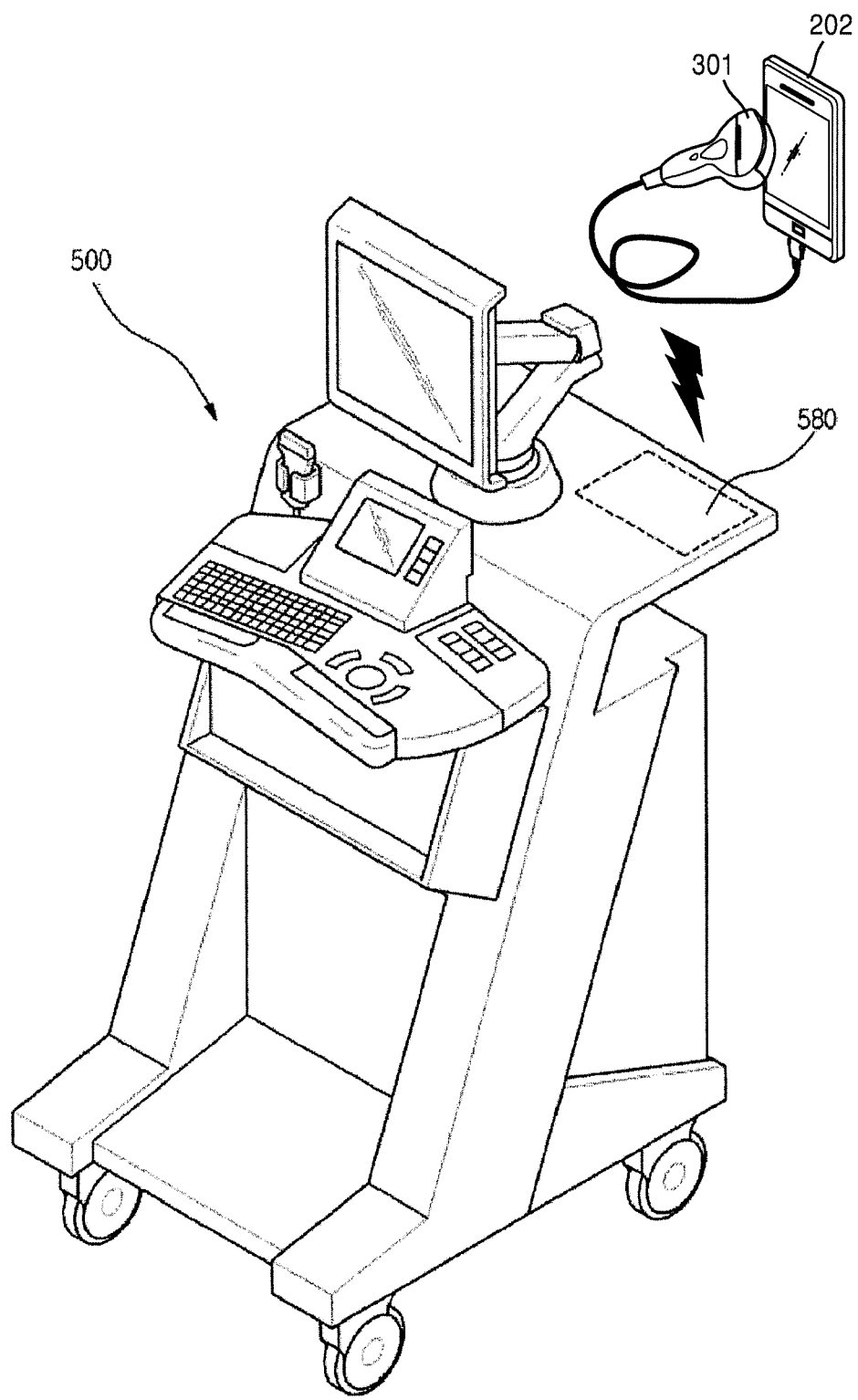

FIG. 5C illustrates an ultrasound diagnostic system in which the portable ultrasound diagnostic device 202 of FIG. 3C is connected to the cart-based ultrasound diagnostic device 500.

The cart-based ultrasound diagnostic device 500 may be connected to the portable ultrasound diagnostic device 202 by using the above-described wireless communication methods. A connection between the cart-based ultrasound diagnostic device 500 and the portable ultrasound diagnostic device 202 via wireless communication corresponds to the connection between the cart-based ultrasound diagnostic device 500 and the portable ultrasound diagnostic device 201 via wireless communication, which is described above with reference to FIG. 5B, and thus a detailed description thereof will be omitted herein.

Figure 6:
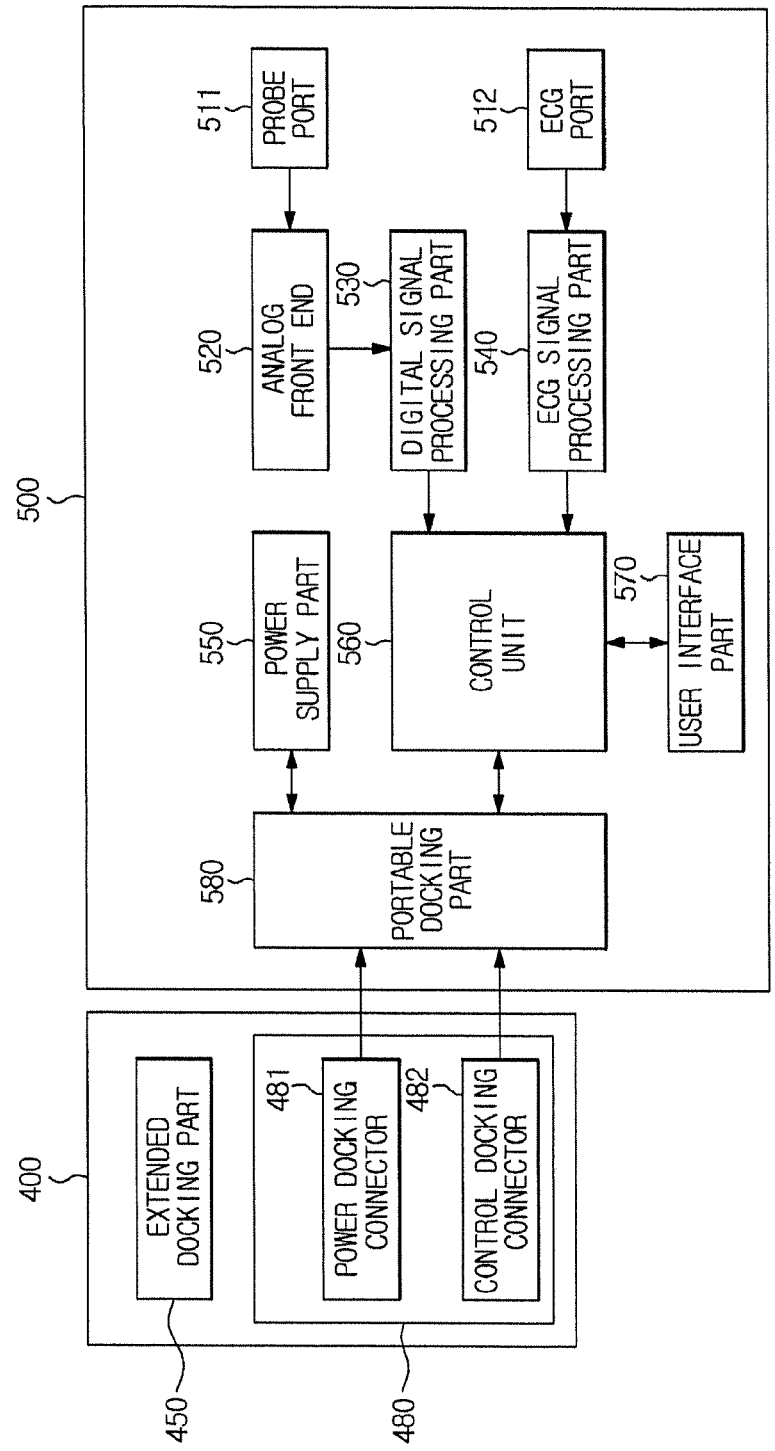
FIG. 6 is a control block diagram illustrating the ultrasound diagnostic system of FIG. 5A.

FIG. 6 is a control block diagram illustrating the ultrasound diagnostic system according to the second embodiment.

Referring to FIG. 6, the ultrasound diagnostic system according to the second embodiment includes the portable ultrasound diagnostic device 400 having the cart-based docking part 480 and the indoor ultrasound diagnostic device 500 having the portable docking part 580.

The portable ultrasound diagnostic device 400 may include an extended docking part 450 so as to be connected with the above-mentioned extended docking device 300. A power docking connector 481 may be separated from a control docking connector 482 as described above, thereby preventing performance deterioration due to noise generation. The portable ultrasound diagnostic device 400 shown in the control block diagram of FIG. 6 illustrates only a portion relative to docking, and no description will be given in conjunction with general functions of the portable ultrasound diagnostic device 400.

The indoor ultrasound diagnostic device 500 includes a probe port 511 connected to an ultrasound probe, an analog front end (AFE) 520 to convert analog signals transmitted from the probe port 511 into digital signals, a digital signal processing part 530 to process the converted digital signals, and a control unit 560 to perform various types of controls within the ultrasound diagnostic device 500 using the processed digital signals. The indoor ultrasound diagnostic device 500 further includes a portable docking part 580 connected to the portable ultrasound diagnostic device 400, a user interface part 570, and a power supply part 550 connected to a power supply unit of the portable ultrasound diagnostic device 400 for charging the power supply unit.

The indoor ultrasound diagnostic device 500 may also include an electrocardiogram (ECG) port 512 so as to measure an electrocardiogram in addition to diagnosis using the probe. The indoor ultrasound diagnostic device 500 enables setting of various modes such as a continuous wave (CW) Doppler mode, a color Doppler mode, or a power Doppler mode so as to analyze an ultrasound image photographed by the portable ultrasound diagnostic device 400 in a desired mode.

The portable ultrasound diagnostic device 400 may be connected or coupled to the indoor ultrasound diagnostic device 500, thereby enabling utilization of various functions of the indoor ultrasound diagnostic device 500. As described above, the ultrasound diagnostic system according to the second embodiment may enhance portability of the portable ultrasound diagnostic device and simultaneously achieves superior ultrasound diagnostic performance and quality also in the portable ultrasound diagnostic device through the extension of the probes, signal channels, diagnostic items, or diagnostic performance, as occasion demands.

As is apparent from the above description, the present invention provides an ultrasound diagnostic system capable of enhancing portability of a portable ultrasound diagnostic device and simultaneously achieves superior ultrasound diagnostic performance and quality also in the portable ultrasound diagnostic device through extension of probes and/or signal channels as occasion demands.

Also, a portable ultrasound diagnostic device may be connected to a cart-based body through a docking device in case of not requiring portability, thereby serving as a high performance ultrasound diagnostic device. On the other hand, the portable ultrasound diagnostic device may be separated from the docking device in case of requiring portability, thereby serving as a portable device.

Furthermore, in the case of connecting a portable ultrasound diagnostic device to a docking device or an indoor ultrasound diagnostic device, a power docking connector may be separated from a control docking connector, thereby preventing performance deterioration due to noise generation.

Furthermore, like the extended docking device 300 described with reference to FIGS. 2 through 3C, the indoor ultrasound diagnostic device 500 may perform a function of extending the number of channels. An indoor ultrasound diagnostic device corresponding to the indoor ultrasound diagnostic device 500 performing the same function as the extended docking device 300 will be described in more detail below with reference to FIGS. 10A and 10B.

Figure 7:
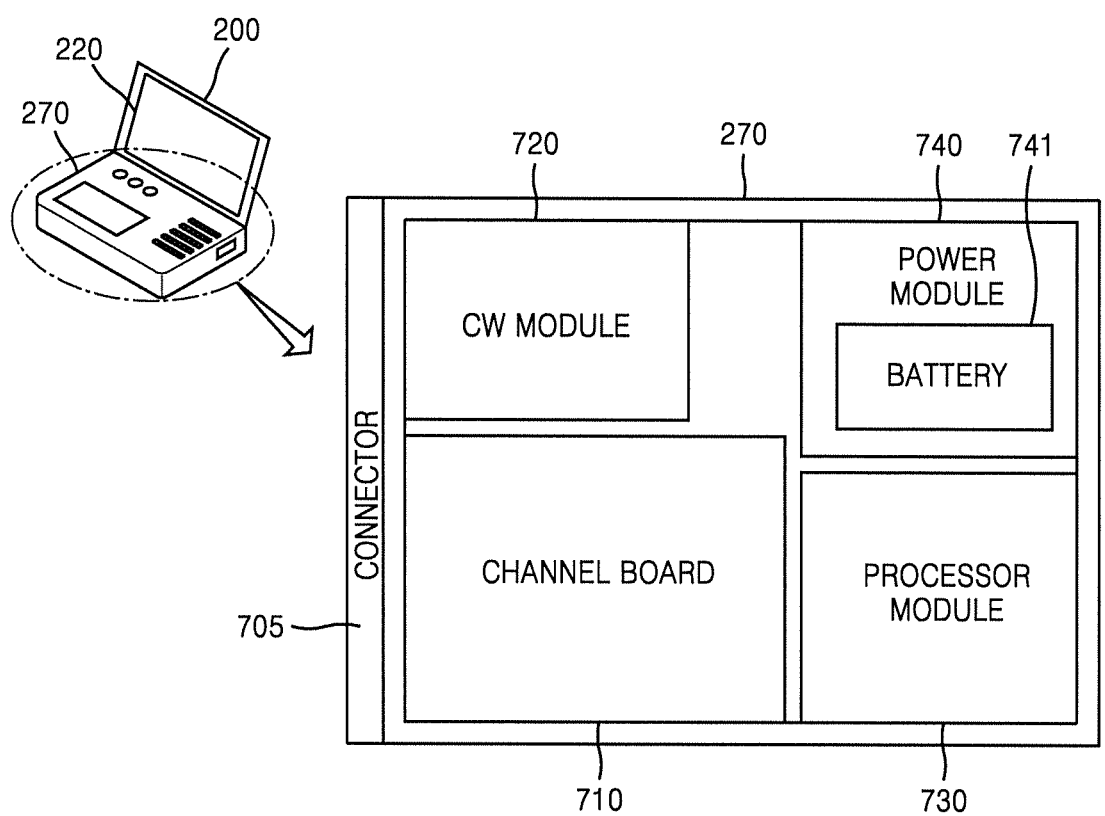
FIG. 7 is a diagram illustrating an internal layout of a portable ultrasound diagnostic device.

FIG. 7 is a diagram illustrating an internal layout of the portable ultrasound diagnostic device 200.

The portable ultrasound diagnostic device 200, as illustrated in FIG. 3A, may include the display part 220 and a lower body 270.

Referring to FIG. 7, elements of the portable ultrasound diagnostic device 200 for imaging an ultrasound image are provided in the lower body 270. For example, a channel board 710, a continuous wave (CW) module 720, a processor module 730, and a power module 740 may be provided as the layout.

The channel board 710 performs a beamforming operation. In detail, the channel board 710 may perform one selected from a transmission beamforming operation and a reception beamforming operation. In detail, the channel board 710 may perform the transmission beamforming operation to generate a plurality of pulse signals, and respectively supply the generated plurality of pulse signals to a plurality of transducer elements corresponding to a plurality of channels. Also, the channel board 710 may perform reception beamforming of a plurality of ultrasound echo signals received from the respective transducer elements.

In detail, the channel board 710 includes an analog front end (AFE) that performs a beamforming operation of converting an analog signal, transmitted from a probe (not shown), into a digital signal. In other words, the channel board 710 may correspond to the AFE 520 described with reference to FIG. 6. The channel board 710 may also be referred to as a beamforming board. In detail, the channel board 710 transmits a pulse signal which is used to generate an ultrasound signal to be transmitted to an object, receives an ultrasound echo signal from the object to scan the object.

The CW module 720 processes a continuous wave used to generate a Doppler mode image. In detail, the CW module may process a continuous-wave pulse to a transducer element to allow a generated ultrasound signal to be transmitted to an object, and receive a continuous-wave ultrasound echo signal from the object to process the received ultrasound echo signal.

The processor module 730 may control an overall operation of the portable ultrasound diagnostic device 200, and generate an ultrasound image. In detail, the processor module 730 may generate, adjust, and control a pulse which is used to generate an ultrasound signal generated by the channel board 710. Also, the processor module 730 may process the ultrasound echo signal received from the channel board 710 or the CW module 720 to generate ultrasound data and/or an ultrasound image.

The power module 740 is charged with power, and supplies power to the internal elements of the portable ultrasound diagnostic device 200 by using the charged power.

The power module 740 may include a battery 741. The battery 741 may be charged with power, and may supply power to the internal elements of the portable ultrasound diagnostic device 200 by using the charged power. The battery 741 may be configured with a rechargeable battery, and when the charged power is discharged, the battery 741 may be again charged with power which is supplied to the battery 741 through a power line (not shown). Also, the battery 731 may be charged with wireless power transmitted from the outside. Also, the power module 740 may directly receive power from the outside through the power line (not shown) to supply power to the internal elements of the portable ultrasound diagnostic device 200.

Moreover, a connector 705 may be provided in at least one side of the portable ultrasound diagnostic device 200, and may include at least one port connected to the probe and a connection terminal connected to an external memory or device.

A size and weight of the portable ultrasound diagnostic device 200 are limited for convenience of carry or movement. As illustrated in FIG. 7, all elements (for example, the channel board 710, the CW module 720, the processor module 730, and the power module 740) which are necessary for imaging an ultrasound image may be disposed in the limited size (area) of the portable ultrasound diagnostic device 200. Therefore, the internal elements of the portable ultrasound diagnostic device 200 may be disposed in the limited area.

Therefore, a size of the channel board 710 may be limited so as to be disposed in the limited area.

Figure 8:
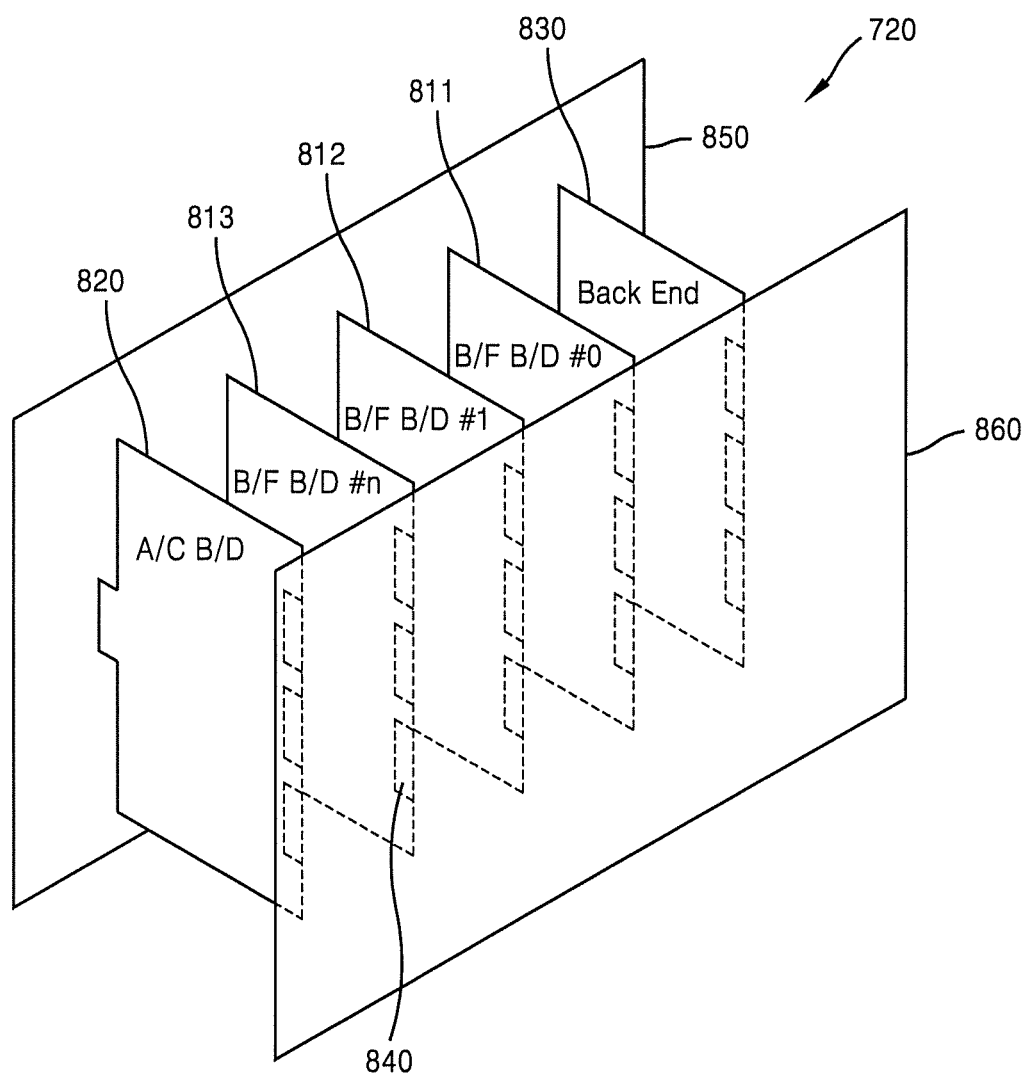
FIG. 8 is a diagram for describing a channel board used in an embodiment of the present invention.

FIG. 8 is a diagram for describing a channel board used in an embodiment of the present invention.

One channel may correspond to one transducer element included in the probe, and a signal received from one transducer element may be referred to as one channel signal. Also, a channel corresponding to a transducer element may be referred to as an element channel.

One signal processed by the channel board 710 may correspond to one channel of the channel board 710, and one channel of the channel board 710 may be referred to as a board channel.

Hereinafter, a channel of the probe is referred to as an element channel, and a channel of the channel board 710 is referred to as a board channel or a channel. Also, a signal which is processed in correspondence with one channel of the channel board 710 is referred to as a channel signal.

In the element channel, the number of element channels may be the same as or different from the number of board channels. For example, when the probe includes 100 transducer elements, 100 ultrasound echo signals respectively received from the 100 transducer elements may be respectively transmitted through 100 element channels. The 100 ultrasound echo signals transmitted through the 100 element channels may be all transferred to the channel board 710, and beamforming of the 100 ultrasound echo signals may be performed in 1:1 through the 100 board channels. As another example, when 100 ultrasound echo signals respectively received from 100 transducer elements respectively correspond to 100 element channels, the channel board 710 may be used in order for one board channel to match four element channels.

Referring to FIG. 8, the channel board 710 may be provided in a board form. In detail, the channel board 710 may include at least one or more channel board units 811 to 813, and each of the channel board units 811 to 813 may process a signal group including at least one channel signal.

For example, one channel board unit (for example, 811) may perform beamforming of 32 signals respectively corresponding to 32 channels. Here, the beamforming include one selected from transmission beamforming and reception beamforming. In detail, the channel board unit 811 may generate 32 pulses respectively corresponding to 32 channels, and perform the reception beamforming of 32 signals to generate pieces of ultrasound data. Also, the number of channels for which beamforming is performed by a channel board unit (for example, 811) may be changed depending on the product specification of the channel board unit.

Referring to FIG. 8, the channel board 710 may include an analog control board 820, the at least one or more channel board units 811 to 813, and a back end board 830.

In detail, each of the at least one or more channel board units 811 to 813 included in the channel board 710 may transmit an ultrasound signal to an object, receive an ultrasound echo signal from the object, transmit an ultrasound signal to each of the transducer elements included in the probe so as to scan the object, receive an ultrasound echo signal from each of the transducer elements, and perform the reception beamforming of the ultrasound echo signal to convert the ultrasound echo signal into a digital signal. In detail, each of the at least one or more channel board units 811 to 813 included in the channel board 710 may respectively transmit a plurality of ultrasound signals to a plurality of transducer elements respectively corresponding to a plurality of element channels, and may respectively receive a plurality of ultrasound echo signals from the plurality of transducer elements respectively corresponding to the plurality of element channels.

In FIG. 8, a case in which the channel board 710 includes three the channel board units 811 to 813 and each channel board unit (for example, 811) receives and processes 32 channel signals will be described as an example. In detail, the channel board unit 811 may process 32 channel signals respectively received from 32 transducer elements among the plurality of transducer elements included in the probe. Here, signal processing performed by the channel board unit 811 may include reception beamforming, which generates an ultrasound signal and transmits the ultrasound signal to a transducer element, and transmission beamforming which receives an ultrasound echo signal from the transducer element and converts the ultrasound echo signal into a digital signal.

Moreover, the number of channel board units included in the channel board and/or the number of channels processible by the channel board units may be changed depending on a setting of a user, the product specification of the portable ultrasound diagnostic device 200, or a setting of a manufacturer of the portable ultrasound diagnostic device 200. However, since the purpose of carrying the portable ultrasound diagnostic device and a size, weight, or volume of the portable ultrasound diagnostic device are limited, enlargement of the channel board 710 is limited, and thus, the number of channels for which beamforming is performed by the channel board 710 is limited.

The analog control board 820 controls the supply of power to the channel board 720 and an operation of the channel board 720.

The back end board 830 may process data received from the channel board units 811 to 813, and transmit the processed data to the processor module 730, which performs imaging of an ultrasound image, through a connection terminal 840.

Moreover, as illustrated, the channel board 720 may be connected to a board 850 for transmitting or receiving a signal to or from the probe. The channel board 720 may transmit or receive a signal to or from the probe through the board 850.

As described above, the channel board 720 may include the channel board units 811 to 813 which have a certain size, volume, or weight, for processing a channel signal received from a transducer element, and thus, the portable ultrasound diagnostic device 200 may include only a limited number of channel board units (for example, 811 to 813). Therefore, the number of channels processible by the channel board 720 included in the portable ultrasound diagnostic device 200 is limited.

In generating an ultrasound image, an image quality of a generated ultrasound signal is determined depending on the number of channels which are simultaneously processible by the channel board 720. For example, when the probe includes 192 transducer elements, the reception beamforming of 192 ultrasound echo signals that are 192 channel signals respectively received from the 192 transducer elements may be performed. In generating an ultrasound image by using the reception-beamforming-performed ultrasound echo signals, when the ultrasound image is generated by using all the 192 ultrasound echo signals respectively corresponding to 192 channels, a quality of the ultrasound image is maximized. On the other hand, when one ultrasound image is generated by performing the reception beamforming of only some of the 192 channel signals respectively received from the 192 transducer elements, a quality of an image is degraded than a quality of an image generated by using all the 192 ultrasound echo signals.

A size of the portable ultrasound diagnostic device 200 is limited for increasing portability. Therefore, in the portable ultrasound diagnostic device 200, the number of channels which are processible at one time is inevitably limited in performing the transmission beamforming of ultrasound echo signals respectively received from the transducer elements included in the probe. Thus, the reception beamforming of only some of the ultrasound echo signals respectively received from the transducer elements included in the probe is inevitably performed once. That is, the portable ultrasound diagnostic device 200 may generally perform the transmission beamforming and reception beamforming of only a limited number of channel signals.

Therefore, a case of increasing a portability of the portable ultrasound diagnostic device 200 and a case of increasing a quality of a generated image by increasing an arrangement space or size of the channel board 720 have a tradeoff relationship, and thus, it is difficult to satisfy two the cases.

An ultrasound system according to an embodiment of the present invention overcomes a limitation of the number of channels, for which the transmission beamforming and the reception beamforming are performed at one time, due to a limitation of the arrangement space of the channel board 720 of the portable ultrasound diagnostic device 200, and by using the docking device, the number of channels for which the transmission beamforming and the reception beamforming are performed at one time increases to more than the number of channels which are processible by the channel board 720 of the portable ultrasound diagnostic device 200. Hereinafter, the ultrasound system according to an embodiment of the present invention will be described in detail with reference to FIGS. 9 to 12.

Figure 9:
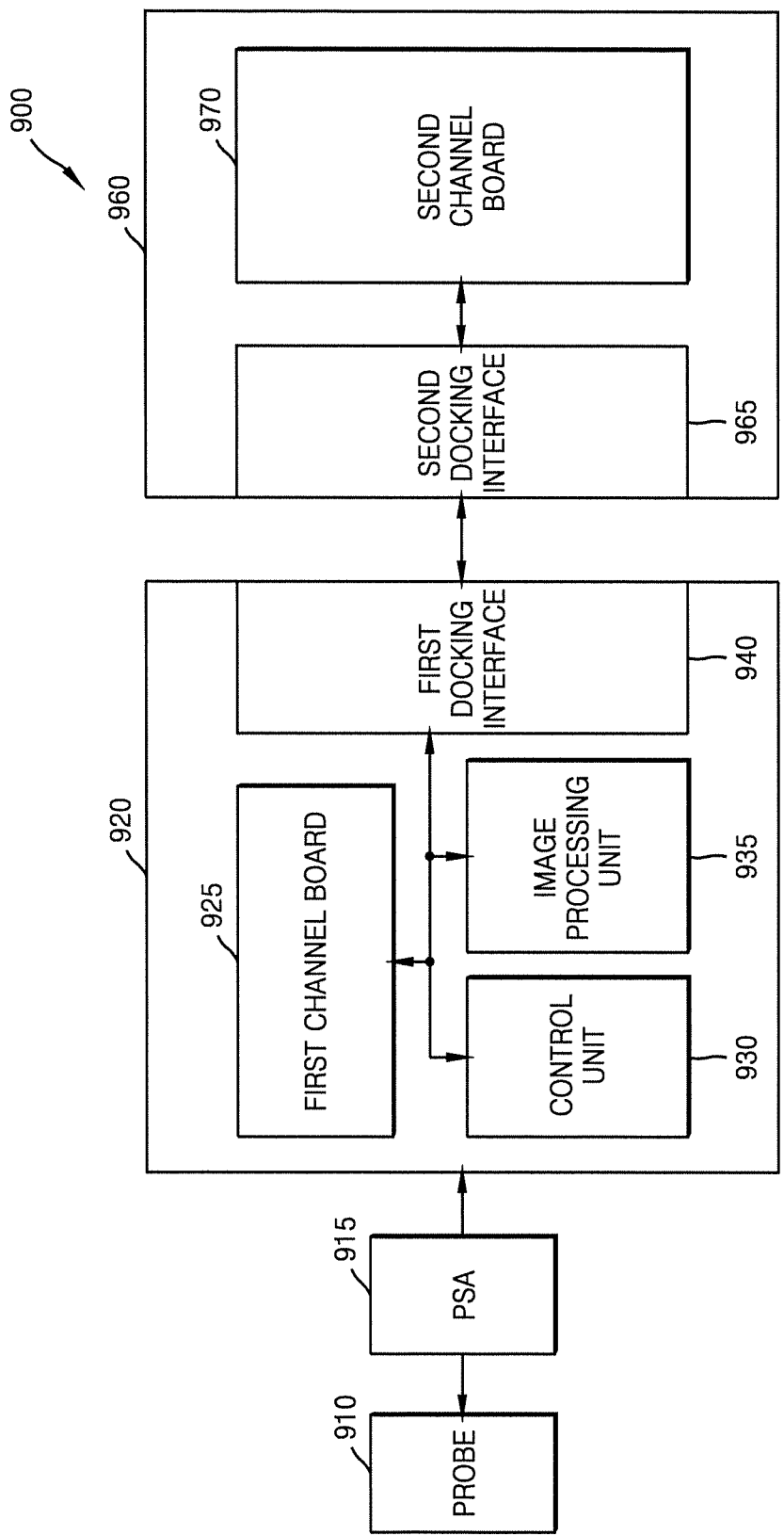
FIG. 9 is a block diagram illustrating an ultrasound diagnostic system according to another embodiment of the present invention.

FIG. 9 is a block diagram illustrating an ultrasound diagnostic system 900 according to another embodiment of the present invention.

The ultrasound diagnostic system 900 according to another embodiment of the present invention includes a probe 910, a portable ultrasound diagnostic device 920, and a docking device 960. In FIG. 9, the probe 910, the portable ultrasound diagnostic device 920, and the docking device 960 respectively correspond to the probes 311 to 315, the portable ultrasound diagnostic device 200, and the extended docking device 300 which have been described above with reference to FIG. 2. Furthermore, the probe 910, the portable ultrasound diagnostic device 920, and the docking device 960 may respectively correspond to the probes 112, 114, or 301, the portable ultrasound diagnostic device 200, 201, 202, or 400, and the indoor ultrasound diagnostic device 500 described with reference to FIGS. 3A through 6. Therefore, a description repetitive of the description of FIGS. 2 through 6 is not provided. Also, the detailed configurations and descriptions of the probe, the portable ultrasound diagnostic device, and the extended docking device (or the indoor ultrasound diagnostic device 500) which have been described above with reference to FIGS. 1 to 6 may be applied to the probe 910, the portable ultrasound diagnostic device 920, and the docking device 960 which are to be described below with reference to FIG. 9.

The probe 910 includes a plurality of transducer elements (not shown). In detail, the probe 910 transmits a plurality of ultrasound echo signals respectively corresponding to a plurality of channels respectively corresponding to the plurality of transducer elements. In detail, the probe 910 transmits the plurality of ultrasound echo signals to the portable ultrasound diagnostic device 920. Here, the probe 910 may transmit ultrasound echo signals, which are equal to or less than the number of the transducer elements, to the portable ultrasound diagnostic device 920 at one time.

Hereinafter, a case in which the number of the transducer elements included in the probe 910 is K number and the number of the ultrasound echo signals transmitted by the probe 910 is N number will be described as an example. Here, K may be equal to or more than N. And, K and N are integer. For example, the probe 910 transmits N number of ultrasound echo signals respectively corresponding to N number of element channels to the portable ultrasound diagnostic device 920. In detail, each of the transducer elements may transmit an ultrasound signal to an object, and receive an echo signal reflected from the object. As described above, each transducer element corresponds to one element channel, and a signal transmitted or received by one transducer element may be referred to as an element channel signal. Here, N may vary depending on the kind of the probe 910. Also, a case in which one element channel corresponds to one board channel so as to match each other in 1:1 will be described below as an example.

The portable ultrasound diagnostic device 920 includes a first channel board 925 that performs beamforming of at least one of signals transmitted or received to or from the plurality of transducer elements. In detail, the first channel board 925 performs a beamforming operation including a selected from a reception beamforming operation and a transmission beamforming operation. Also, the portable ultrasound diagnostic device 920 may include a first docking interface 940 for transmitting or receiving certain data to or from the docking device 960.

The docking device 960 includes a second channel board 970. The second channel board 970 may perform the same function as that of the first channel board 925, and in detail, perform the reception beamforming operation and the transmission beamforming operation. In other words, the second channel board 970 for performing the transmission beamforming operation and the reception beamforming operation may correspond to the AFE 520 for performing a beamforming operation in the indoor ultrasound diagnostic device 500 of FIG. 6. Furthermore, the docking device 960 may be the indoor ultrasound diagnostic device 500 described with reference to FIGS. 5A through 6. In this case, the AFE 520 of the indoor ultrasound diagnostic device 500 may correspond to the second channel board 970. The portable ultrasound diagnostic device 920 is detachably attached to the docking device 960. Alternatively, the docking device 960 may be connected wirelessly to the portable ultrasound diagnostic device 920 by using the above-described WLAN, WI-FI, Bluetooth, Zigbee, WFD, IrDA, BLE, NFC, Wibro, WiMAX, SWAP, WiGig, RF communication, etc.

Moreover, the docking device 960 may include a second docking interface 965. Here, the second docking interface 965 allows data to be transmitted or received to or from the portable ultrasound diagnostic device 920. Also, the second docking interface 965 may correspond to the docking interface 301 of FIG. 2. Also, the second docking interface 965 may correspond to the portable docking part 580 of FIG. 6.

Furthermore, the probe 910 may be formed integrally with the portable ultrasound diagnostic device 920. In other words, when the portable ultrasound diagnostic device 920 corresponds to the portable ultrasound diagnostic device 201 of FIG. 3B, the probe 910 including a plurality of transducer elements may be formed integrally with the portable ultrasound diagnostic device 920 and be implemented in a portable form. Furthermore, in this case, the portable ultrasound diagnostic device 920 may be connected to the docking device 960 through wired or wireless communication. In addition, when the portable ultrasound diagnostic device 920 corresponds to the portable ultrasound diagnostic device 202 of FIG. 3C, the portable ultrasound diagnostic device 920 may be connected to the docking device 960 through wired or wireless communication. In the above-described configuration, the first and second docking interfaces 940 and 965 may each include a wired communication interface (not shown) and/or a wireless communication interface (not shown) for performing wired and/or wireless communication.

For example, the wireless communication interface may include at least one communication module (not shown) for performing wireless communication according to at least one from among short-range data communication methods including 60 Hz mmWave WLAN, WI-FI, Bluetooth, Zigbee, WFD, IrDA, BLE, NFC, Wibro, WiMAX, SWAP, WiGig, and RF communication.

Moreover, the first channel board 925 may perform beamforming by using a less number of channels than the number of transducer elements included in the probe 910.

Moreover, the second channel board 970 may perform beamforming by using channels equal to the number of transducer elements included in the probe 910.

Moreover, the second channel board 970 may perform beamforming by using channels equal to the number of signals transmitted or received by the probe 910 and the portable ultrasound diagnostic device 910.

Moreover, the second channel board 970 may perform beamforming of signals, for which beamforming is not performed by the first channel board 925, among a plurality of signals transmitted or received to or from the plurality of transducer elements included in the probe 910.

Moreover, the number of signals for which beamforming is performed by the second channel board 970 may be greater than the number of signals for which beamforming is performed by the first channel board 925.

Hereinafter, an operation will be described in which at least one of the first and second channel boards 925 and 970 performs beamforming of signals transmitted or received by the plurality of transducer elements included in the probe 910.

In detail, the portable ultrasound diagnostic device 920 includes the first channel board 925 that receives and collects at least one of a plurality of ultrasound echo signals transmitted from the probe 910. Hereinafter, a case in which the number of ultrasound echo signals receivable and collectable by the first channel board 925 is a maximum of M number and M is less than N that is the number of ultrasound echo signals transmitted from the probe 910 will be described as an example. That is, the first channel board 925 may receive and collect ultrasound echo signals which are less than M number and are some of the plurality of ultrasound echo signals transmitted from the probe 910. In detail, the portable ultrasound diagnostic device 920 includes the first channel board 925 that receives and collects M number of ultrasound echo signals, which are less than N number, among N number of ultrasound echo signals transmitted from the probe 910. In detail, the portable ultrasound diagnostic device 920 may receive a plurality of ultrasound echo signals respectively corresponding to a plurality of channels from the probe 910, acquire pieces of ultrasound data respectively corresponding to the plurality of channels by performing the reception beamforming of the plurality of ultrasound echo signals, and generate an ultrasound image by using the acquired pieces of ultrasound data.

Furthermore, when the docking device 960 corresponds to the indoor ultrasound diagnostic device 500, the docking device 960 may further include the digital signal processing part 530 and the control unit 560 of the indoor ultrasound diagnostic device 500 described with reference to FIG. 6. In this case, the docking device 960 may acquire pieces of ultrasound data by performing beamforming via at least one of the first and second channel boards 925 and 970 and generate an ultrasound image based on the acquired pieces of ultrasound data. In other words, an operation of generating an ultrasound image that is performed by the portable ultrasound diagnostic device 920 may be performed by the docking device 960 as well. In detail, an ultrasound image may be generated using at least one of the digital signal processing part 530 and the control unit 560 included in the docking device 960.

Hereinafter, as described above, a case in which the probe 910 transmits N number of ultrasound echo signals to the portable ultrasound diagnostic device 920 and the number of channel signals processible by the first channel board 925 is a maximum of M number will be described as an example. Also, a case in which the second channel board 970 processes (for example, performs the reception beamforming and/or the transmission beamforming) some of N number of ultrasound echo signals transmitted from the probe 910 to the portable ultrasound diagnostic device 920 will be described as an example.

In detail, the first channel board 925 performs the transmission beamforming operation and the reception beamforming operation. In detail, the first channel board 925 performs the transmission beamforming operation to generate M number of ultrasound signals respectively corresponding to M number of channels, supplies the M ultrasound signals to the probe 910, and performs the reception beamforming of M number of ultrasound echo signals, which are less than N number, among N number of ultrasound echo signals transmitted from the probe 910.

In detail, the second channel board 970 receives at least one ultrasound echo signal corresponding to at least one channel among the N ultrasound echo signals transmitted from the probe 910, and collects the received at least one ultrasound echo signal.

Moreover, the second channel board 970 is not limited in space and size unlike the potable ultrasound diagnostic device 920, and thus may include more channel board units than the portable ultrasound diagnostic device 920. Also, the second channel board 970 may be provided as a channel board which has greater volume and size than those of the portable ultrasound diagnostic device 920.

Therefore, the second channel board 970 can perform, at one time, the reception beamforming and transmission beamforming of more signals compared to the first channel board 925 included in the portable ultrasound diagnostic device 920.

Here, the docking device 960 is a cart-based device, and is not limited in size unlike the portable ultrasound diagnostic device 920. Therefore, the second channel board 970 included in the docking device 960 may include the at least one or more channel board units 811 to 813 so as to perform the reception beamforming and transmission beamforming of signals respectively corresponding to more channels compared to the first channel board 925.

In detail, each of the transducer elements included in the probe 910 transmits an ultrasound signal to an object according to a driving signal applied from the portable ultrasound diagnostic device 920, and receives an echo signal reflected from the object. The probe 910 includes a plurality of transducer elements, which vibrate according to an electrical signal applied thereto to generate an ultrasound wave that is sound energy. Also, the probe 910 may be connected to the portable ultrasound diagnostic device 920 or the docking device 960 by using wired or wireless communication. Also, a plurality of probes may be connected to the portable ultrasound diagnostic device 920 and/or the docking device 960 depending on an implementation type of the ultrasound system 900.

Moreover, the probe 910 may be connected to the portable ultrasound diagnostic device 920 and/or the docking device 960. In FIG. 2, a case in which the plurality of probes 311 to 315 are connected to the extended docking device 300 is illustrated as an example. In FIG. 9, a case in which the probe 910 is connected to the portable ultrasound diagnostic device 920 is illustrated as an example.

Moreover, the probe 910 may include K number of transducer elements more than N number that is the number of channel signals which are transmitted from the probe 910 to the portable ultrasound diagnostic device 920 at one time. Here, N and K are natural numbers. In detail, the probe 910 may transmit an ultrasound echo signal to a probe selective assembly (PSA) 915.

The PSA 915 may be included in the portable ultrasound diagnostic device 920. In detail, the PSA 915 may be disposed at a probe connection terminal (not shown) of the portable ultrasound diagnostic device 920. When the PSA 915 is included in the portable ultrasound diagnostic device 920, an ultrasound echo signal transmitted from the probe 910 may be transmitted to a control unit 930 or the first channel board 925 of the portable ultrasound diagnostic device 920 through the PSA 915.

Moreover, the PSA 915 may be included in the docking device 960. When the PSA 915 is included in the docking device 960, the at least one or more probe ports 321 to 325 illustrated in FIG. 3A may be included in the PSA 915. When the PSA 915 is included in the docking device 960, an ultrasound echo signal transmitted from the probe 910 may be transmitted to a control unit (not shown in FIGS. 9 and 1080 of FIG. 10A) and the second channel board 970 of the docking device 960 through the PSA 915. And the control unit of the docking device 960 may control transmission of at least one of ultrasound echo signal which does not processed by the second channel board 970 to the portable ultrasound diagnostic device 920.

Hereinafter, a case in which the PSA 915 is included in the portable ultrasound diagnostic device 920 and is disposed at the probe connection terminal (not shown) of the portable ultrasound diagnostic device 920 is illustrated as an example. A configuration and operation of the PSA 915 will be described below in detail with reference to FIG. 11.

The PSA 915 transmits, at one time, N number of ultrasound echo signals among K number of ultrasound echo signals respectively received from K number of transducer elements included in the probe 910. In detail, the PSA 915 may parallelly transmit, to the control unit 930 of the portable ultrasound diagnostic device 920, the N ultrasound echo signals among the K ultrasound echo signals respectively received from the K transducer elements and signals other than the N ultrasound echo signals among the K ultrasound echo signals.

For example, the PSA 915 may receive K number of ultrasound echo signals respectively corresponding to K number of channels from K number of transducer elements, may first transmit N number of ultrasound echo signals among the K ultrasound echo signals to the portable ultrasound diagnostic device 920 (for example, the control unit 930 of the portable ultrasound diagnostic device 920), and may subsequently transmit K-N number of ultrasound echo signals to the portable ultrasound diagnostic device 920. Then, the portable ultrasound diagnostic device 920 may receive and collect the first-transmitted N ultrasound echo signals by using all the first and second channel boards 925 and 970 or by using the second channel board 970. The portable ultrasound diagnostic device 920 may receive and collect the subsequently-transmitted K-N ultrasound echo signals by using all the first and second channel boards 925 and 970 or by using the second channel board 970. The detailed reception and collection of ultrasound echo signals transmitted from the probe 910 will be described below in detail with reference to FIGS. 10A through 11.

Furthermore, when the portable ultrasound diagnostic device 920 corresponds to the portable ultrasound diagnostic device 201 or 202 described with reference to FIG. 3B or 3C, the portable ultrasound diagnostic device 920 may not include the PSA 915. In this case, the probes 112 and 114 may each transmit at least one of the K number of ultrasound echo signals directly to the first channel board 925 of the portable ultrasound diagnostic device 920. In addition, the control unit 930 of the portable ultrasound diagnostic device 920 may control at least one of the K number of ultrasound echo signals acquired by the probe 112 or 114 to be transmitted to the second docking interface 965 of the docking device 960 via the first docking interface 940.

In detail, the portable ultrasound diagnostic device 920 may further include the control unit 930, an image processing unit 935, and the first docking interface 940, in addition to the first channel board 925.

The control unit 930 controls an overall operation of the portable ultrasound diagnostic device 920 for imaging an ultrasound image. That is, the control unit 930 may control operations of the probe 910, the first channel board 925, the image processing unit 935, and the first docking interface 940.

The image processing unit 935 may receive at least one ultrasound echo signal received and collected by the second channel board 970, and generate an ultrasound image by using M or more number of ultrasound echo signals and the at least one ultrasound echo signal received and collected by the second channel board 970.

In detail, the image processing unit 925 generates a pulse which is used for the first channel board 925 and/or the second channel board 970 to generate an ultrasound signal, and transmits the generated pulse to the first channel board 925 and/or the second channel board 970. Furthermore, the image processing unit 925 may generate pieces of ultrasound data by using a plurality of ultrasound echo signals which are transmitted from the probe 910 and for which the reception beamforming is performed by the first channel board 925 and/or the second channel board 970, and generate an ultrasound image by using the generated pieces of ultrasound data.

When the portable ultrasound diagnostic device 920 is equipped in the docking device 960, the first docking interface 940 interfaces data transmitted or received between the portable ultrasound diagnostic device 920 and the docking device 960. For example, the first docking interface 940 may transmit a generation request of at least one pulse, which is to be applied to the probe 910, to the second docking interface 965 according to control by the control unit 930. Hereinafter, the generation request of the at least one pulse which is to be applied to the probe 910 is referred to as a transmission beamforming request. The second channel board 970 generates at least one pulse which is to be applied to at least one transducer element of the probe 910, based on the transmission beamforming request transmitted to the second docking interface 965. The at least one pulse generated by the second channel board 970 is transmitted to the first docking interface 940 through the second docking interface 965. Furthermore, the at least one pulse received by the first docking interface 940 is transmitted to the probe 910 according to control by the control unit 930. The probe 910 applies the transmitted at least one pulse to at least one transducer element that is a piezoelectric vibrator. Therefore, that transducer element may generate an ultrasound signal corresponding to the applied pulse, and transmit the ultrasound signal to an object.

Moreover, the first docking interface 940 may transmit or receive certain data to or from the docking interface 301 corresponding to the second docking interface 965. Also, the first docking interface 940 may correspond to the extended docking part 250 of FIG. 4. Also, the first docking interface 940 may correspond to the cart-based docking part 480 of FIG. 6. Furthermore, as described above, the first docking interface 940 may include the wired or wireless communication interface for performing wired or wireless communication with the docking device 960.

Moreover, in applying N number of ultrasound signals corresponding to N number of channels to the probe 910 at one time, the second channel board 970 may generate at least one pulse corresponding to at least one of the N channels, and the first channel board 925 may generate a pulse corresponding to each of the other channels, which are not processed by the second channel board 970, among the N channels.

The plurality of transducer elements included in the probe 910 may respectively receive a plurality of ultrasound echo signals from an object, and transmit N number of ultrasound echo signals respectively corresponding to N number of channels among the received plurality of ultrasound echo signals to the portable ultrasound diagnostic device 920 at one time. The control unit 930 may perform control in order for the reception beamforming of the received N ultrasound echo signals to be performed by the first and second channel boards 925 and 970 or the second channel board 970. The image processing unit 935 may generate an ultrasound image by using the reception-beamforming-performed N ultrasound echo signals.

For example, it is assumed that N=128, and it is assumed that the portable ultrasound diagnostic device 920 may 128 pulses respectively corresponding to 128 channels to the probe 910 at one time, and receive 128 ultrasound echo signals respectively corresponding to the 128 channels from the probe 910 at one time. Also, it is assumed that the number of signal channels for which the transmission beamforming and the reception beamforming are performed by the first channel board 925 included in the portable ultrasound diagnostic device 920 is 64.

In this case, when N is 128 and the portable ultrasound diagnostic device 920 applies the 128 pulses respectively corresponding to the 128 channels to the probe 910 at one time, 64 pulses may be generated by the first channel board 925, and the other 64 pulses may be generated by the second channel board 970. Furthermore, the 128 ultrasound echo signals respectively corresponding to the 128 channels among a plurality of ultrasound echo signals received by the probe 910 are transmitted to the portable ultrasound diagnostic device 920 at one time. Then, the control unit 930 of the portable ultrasound diagnostic device 920 may perform control so that the first channel board 925 performs the reception beamforming of the 64 ultrasound echo signals, and the second channel board 970 performs the reception beamforming of the other 64 ultrasound echo signals. The image processing unit 935 may generate an ultrasound image by using pieces of ultrasound data which are generated by performing the reception beamforming of the 128 ultrasound echo signals in the first and second channel boards 925 and 970 and respectively correspond to the 128 channels.

As another example, N is 128, 128 pulses may be all generated by the second channel board 970, and the first channel board 925 may not generate any pulse. The 128 ultrasound echo signals respectively corresponding to 128 channels among a plurality of ultrasound echo signals received by the probe 910 are transmitted to the portable ultrasound diagnostic device 920 at one time. Then, the control unit 930 of the portable ultrasound diagnostic device 920 may perform control so that the second channel board 970 performs the reception beamforming of all the 128 ultrasound echo signals. The image processing unit 935 may generate an ultrasound image by using pieces of ultrasound data which are generated by performing the reception beamforming of the 128 ultrasound echo signals in the second channel board 970 and respectively correspond to the 128 channels.

As described above, by using the second channel board 970 included in the docking device 960, the ultrasound system 900 according to another embodiment of the present invention increases the number of signal channels, which are processed by the portable ultrasound diagnostic device 920 at one time, to N=128 exceeding M=64. Accordingly, the portable ultrasound diagnostic device 920 generates a high-quality ultrasound image.

Moreover, the portable ultrasound diagnostic device 920 may be detachably attached to the ultrasound system 900 so as to carry and use the portable ultrasound diagnostic device 920. Also, the portable ultrasound diagnostic device 920 may be equipped in the docking device 960 so as to generate a high-quality ultrasound image.

Moreover, the docking device 960 may include only the channel board and the elements (for example, the power module and the like) necessary for performing the reception beamforming operation and the transmission beamforming operation, and thus may not be configured with high-specification and high-cost equipment. Therefore, although the low-cost docking device 960 is used, a high-specification ultrasound device may be implemented with the portable ultrasound diagnostic device 920.

Furthermore, when the docking device 960 corresponds to the indoor ultrasound diagnostic device 500, the indoor ultrasound diagnostic device 500 (in detail, corresponding to the second channel board 970) may use the AFE 520 included therein to generate a high quality ultrasound image based on ultrasound signals acquired by the probe 910 connected to the portable ultrasound diagnostic device 920. In other words, the indoor ultrasound diagnostic device 500 may operate to generate a high quality ultrasound image by using the AFE 520 included therein even when it does not include an additional component or module.

As described above, the ultrasound diagnostic system 900 may perform beamforming of at least some of signals transmitted or received by the probe 910 by using the second channel board 970, and thus increases the number of signal channels processible by the portable ultrasound diagnostic device 920. Accordingly, a quality of an ultrasound image generated by the portable ultrasound diagnostic device 920 increases.

Figure 10A:
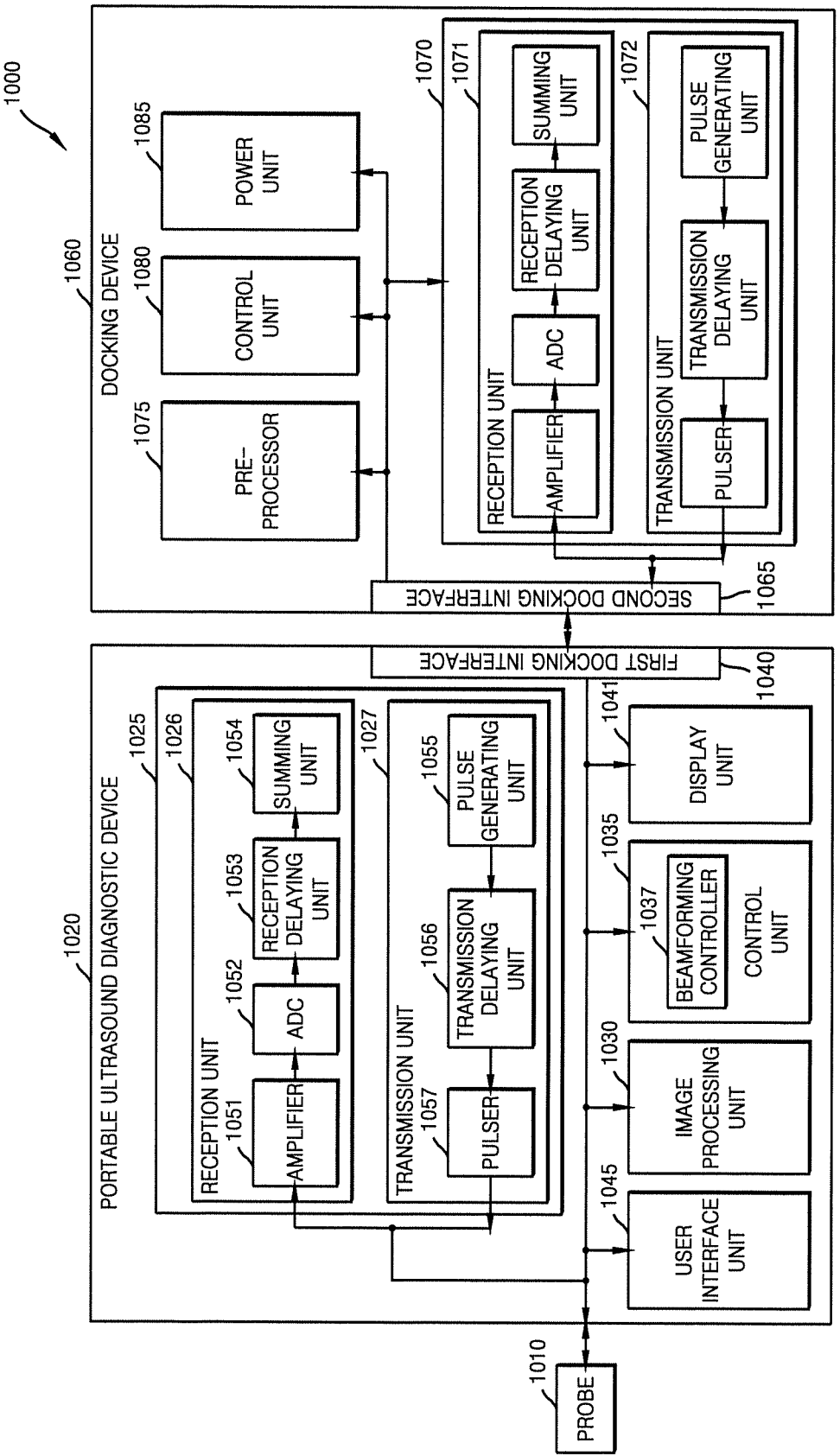
FIGS. 10A and 10B are block diagrams illustrating ultrasound diagnostic systems according to other embodiments.

FIG. 10A is a block diagram illustrating an ultrasound diagnostic system 1000 according to another embodiment of the present invention.

Referring to FIG. 10A, the ultrasound diagnostic system 1000 includes a probe 1010, a portable ultrasound diagnostic device 1020, and a docking device 1060. In FIG. 10A, the probe 1010, the portable ultrasound diagnostic device 1020, and the docking device 1060 respectively correspond to the probe 910, the portable ultrasound diagnostic device 920, and the docking device 960 which have been described above with reference to FIG. 9. Therefore, a description repetitive of the description of FIG. 9 is not provided. In detail, in FIGS. 9 and 10A, the same names refer to the same elements. For example, first and second docking interfaces 1040 and 1065 shown in FIG. 10A may respectively correspond to the first and second docking interfaces 940 and 965 described with reference to FIG. 9.

Referring to FIG. 10A, a first channel board 1025 may include at least one channel board unit that processes at least one signal channel and has been described above with reference to FIG. 8. In FIG. 10A, a case in which the first channel board 1025 is configured with one channel board unit 1025 is illustrated.

In detail, the channel board unit 1025 may include a reception unit 1026 and a transmission unit 1027.

The transmission unit 1027 performs the transmission beamforming operation to supply a pulse for driving a transducer element. In detail, the transmission unit 1027 may generate a plurality of pulses respectively corresponding to a plurality of channels, and may respectively apply a plurality of pulses to a plurality of transducer elements.

The reception unit 1026 may perform the reception beamforming operation to receive and collect the ultrasound echo signal from the transducer element. In detail, the reception unit 1026 may receive a plurality of ultrasound echo signals respectively corresponding to the plurality of channels from the plurality of transducer elements, and receive and collect the received plurality of ultrasound echo signals to generate pieces of ultrasound data.

In detail, the transmission unit 1027 supplies a driving signal to the probe 1010 and includes a pulse generating unit 1055, a transmission delaying unit 1056, and a pulser 1057. The pulse generating unit 1055 generates pulses for forming transmission ultrasound waves based on a predetermined pulse repetition frequency (PRF), and the transmission delaying unit 1056 applies a delay time for determining transmission directionality to the pulses. Pulses to which a delay time is applied correspond to a plurality of piezoelectric vibrators included in the probe 1010, respectively. The pulser 1057 applies a driving signal (or a driving pulse) to the probe 1010 as a timing corresponding to each pulse to which a delay time is applied. In detail, the driving signal is applied to the transducer element included in the probe 1010.

The reception unit 1026 generates ultrasound data by processing echo signals received from the probe 1010 and may include an amplifier 1051, an analog-digital converter (ADC) 1052, a reception delaying unit 1053, and a summing unit 1054. The amplifier 1051 amplifies echo signals in each channel, and the ADC 1052 analog-digital converts the amplified echo signals. The reception delaying unit 1053 applies delay times for determining reception directionality to the digital-converted echo signals, and the summing unit 1054 generates ultrasound data by summing the echo signals processed by the reception delaying unit 1053. Also, according to embodiments of the present invention, the reception unit 1026 may not include the amplifier 1051. In other words, if sensitivity of the probe 1010 or the capability to process bit by the ADC 1052 were enhanced, the amplifier 1051 may be omitted.

In detail, the image processing unit 1030 generates an ultrasound image by scan-converting pieces of ultrasound data received from the first and second channel boards 1025 and 1027 or pieces of ultrasound data received from the second channel board 1070. Meanwhile, an ultrasound image may include not only a grayscale ultrasound image obtained by scanning a target object in an amplitude (A) mode, a brightness (B) mode, and a motion (M) mode, but also a blood flow Doppler image showing flow of blood (aka a color Doppler image), a tissue Doppler image showing movement of tissues, and a spectral Doppler image showing moving speed of a target object as a waveform.

Moreover, the image generating unit 1030 may generate a 3-dimensional (3D) ultrasound image via volume-rendering of volume data and may also generate an elasticity image which visualizes deformation of an object due to a pressure. Furthermore, the image generating unit 1030 may display various pieces of additional information in an ultrasound image by using texts and graphics. Meanwhile, the generated ultrasound image may be stored in a memory (not shown) included in the portable ultrasound diagnostic device 1020.

The control unit 1035 may include a beamforming controller 1037. The beamforming controller 1037 may control the transmission beamforming operation and reception beamforming operation of the first channel board 1025. For example, in performing the transmission beamforming and the reception beamfoming on N number of signals equal to the number of ultrasound signals and ultrasound echo signals which are transmitted or received to or from the probe 1010 at one time, the beamforming controller 1037 may perform control so that the second channel board 1070 performs the transmission beamforming and reception beamforming of at least one of the signals. For example, the number of channels processed by the second channel board 1070 may be autonomously set by the beamforming controller 1037.

A display unit 1041 displays a certain screen according to control by the control unit 1035. In detail, the display unit 1041 may include a display panel (not shown), and display a user interface screen and a medical image screen in the display panel. In detail, the display unit 1041 may display an ultrasound image generated by the image processing unit 1030.

A user interface unit 1045 may generate and output the user interface screen for receiving a command or data from a user. Also, the user interface unit 1045 receives the command or the data from the user through the user interface screen. The user may recognize certain information by looking at the user interface screen displayed by the display unit 1041, and input the command or the data through the user interface unit 1045.

For example, the user interface unit 1045 may include a mouse, a keyboard, or an input device which includes hard keys for inputting data. For example, the user may manipulate at least one selected from the mouse, the keyboard, or the other input device included in the user interface unit 1045 to input the data or the command.

As another example, the user interface unit 1045 may be configured with a touch pad. In detail, the user interface unit 1045 may include the touch pad (not shown) which is coupled to the display panel (not shown) included in the display unit 1041. In this case, the user interface screen is output by the display panel. When a command is input through the user interface screen, the touch pad senses the command, and transmits sensed information. Then, the control unit 1035 may analyze the sensed information to recognize and execute the command input from the user.

In detail, in a case where the user interface unit 1045 is configured with the touch pad, when the user touches a position of the user interface screen, the user interface unit 1045 senses the touched position. The user interface unit 1045 may transmit sensed position information to the control unit 1035. Then, the control unit 1035 may recognize a request received from the user corresponding to a menu displayed at the sensed position, and execute the recognized request.

In detail, the display unit 1041 may display a menu screen for determining signals, processed by the second channel board 1070, among N number of signals for which the transmission beamforming and the reception beamforming are performed at one time. The user may set the signals, processed by the second channel board 1070, among the N signals through the user interface unit 1045. For example, the user may request, through the user interface unit 1045, that processing be performed by only the second channel board 1070. As another example, the user may request, through the user interface unit 1045, that only signals corresponding to channels more than the number of channels processible by the first channel board 1025 be processed by the second channel board 1070. Also, the user may separately set the number of channels processed by the first channel board 1025 and the number of channels processed by the second channel board 1070 through the user interface unit 1045.

Moreover, in the portable ultrasound diagnostic device 1020, the first channel board 1025 may be disposed in the channel board 710 region described above with reference to FIG. 7, and the image processing unit 1030 and the control unit 1035 may be included in the processor module 730. Also, although not shown in FIG. 10A, the portable ultrasound diagnostic device 1020 may further include the power module 740 described above with reference to FIG. 7, a memory (not shown), and a communication unit (not shown). Elements, which are included in the portable ultrasound diagnostic device 1020 but are not described with reference to FIG. 10A, will be described in detail with reference to FIG. 12.

The docking device 1060 may further include the second channel board 1070, a pre-processor 1075, and a control unit 1080.

The pre-processor 1075 may pre-process at least one ultrasound echo signal received and collected by the second channel board 1070, and transmit the pre-processed ultrasound echo signal to the portable ultrasound diagnostic device 1020. In detail, the pre-processor 1075 may adjust a gain of the at least one ultrasound echo signal received and collected by the second channel board 1070, perform a filtering operation such as a noise removing operation, and perform digital signal processing for converting a signal into a type suitable for transmitting the signal to the portable ultrasound diagnostic device 1020.

The control unit 1080 may control an overall operation of each element of the docking device 1060. In detail, the control unit 1080 may control the transmission beamforming operation and reception beamforming operation of the second channel board 1070.

A detailed configuration of the second channel board 1070 is the same as that of the first channel board 1025, and thus, its detailed description is not provided.

A power unit 1085 supplies power to internal elements by using power supplied from the inside or the outside. The power unit 1085 corresponds to the power module 740 described above with reference to FIG. 7, and thus, its detailed description is not provided.

Figure 10B:
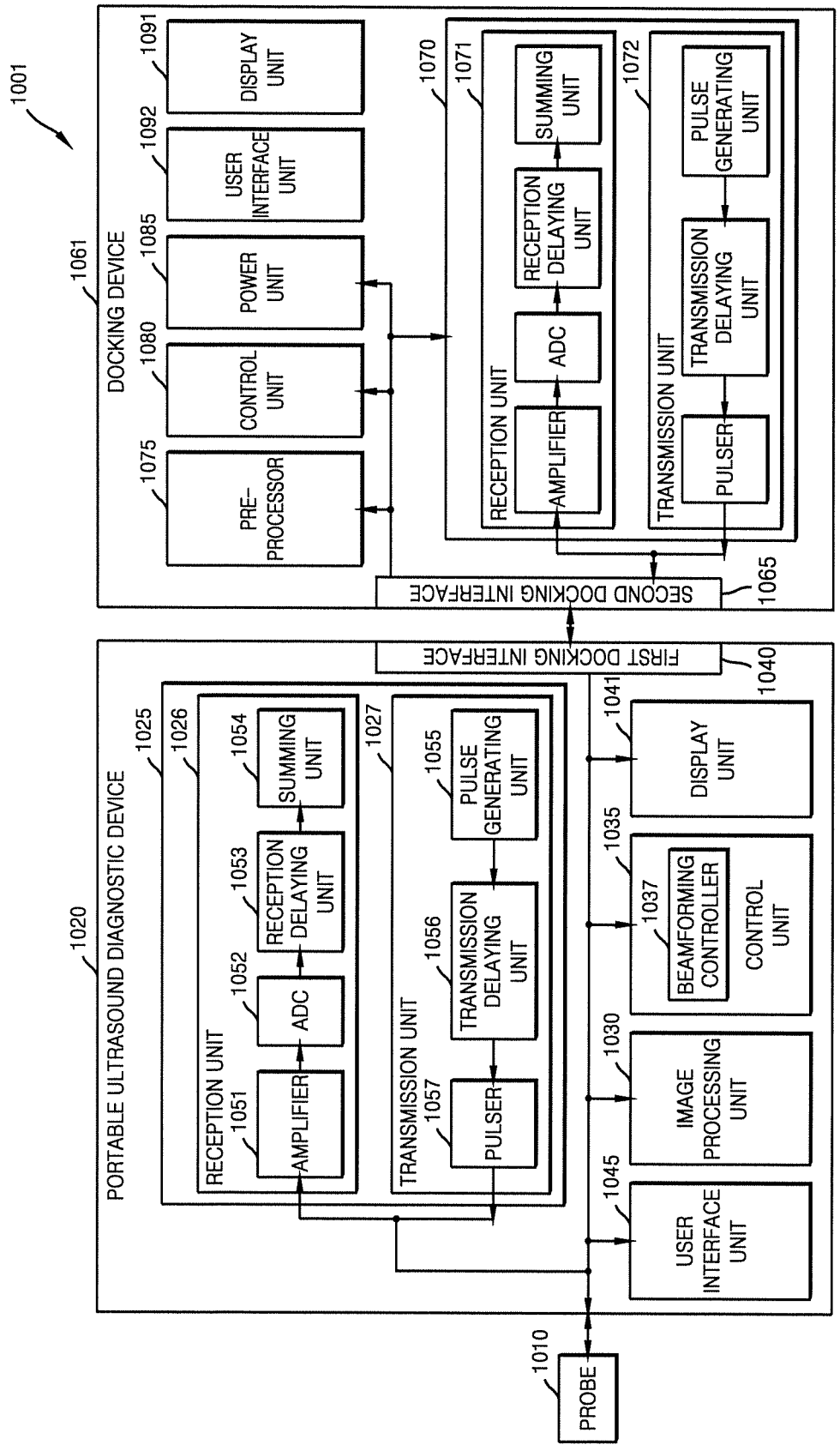

FIG. 10B is a block diagram of a configuration of an ultrasound diagnostic system 1001 according to another embodiment. In FIG. 10B, the same components as those shown in FIG. 10A are denoted by the same reference numerals. Thus, descriptions of the ultrasound diagnostic system 1001 that are already provided above with respect to FIG. 10A will be omitted hereafter.

Referring to FIG. 10B, the ultrasound diagnostic system 1001 includes a probe 1010, a portable ultrasound diagnostic device 1020, and an indoor ultrasound diagnostic device 1061. In this case, the indoor ultrasound diagnostic device 1061 may correspond to the indoor ultrasound diagnostic device 500 described with reference to FIG. 5A through 6. When the indoor ultrasound diagnostic device 1061 corresponds to the indoor ultrasound diagnostic device 500, a second docking device 1065, a second channel board 1070, a processor 1075, a control unit 1080, and a power unit 1085 may respectively correspond to the portable docking part 580, the AFE 520, the digital signal processing part 530, the control unit 560, and the power supply part 550 described with reference to FIG. 6. Furthermore, unlike the indoor ultrasound diagnostic device 500, the indoor ultrasound diagnostic device 1061 may further include a display unit 1091 and a user interface unit 1092. Thus, descriptions of the ultrasound diagnostic system 1001 of FIG. 11, which are already provided above with respect to FIGS. 5A through 6, will be omitted below.

Furthermore, the indoor ultrasound diagnostic device 1061 of FIG. 10B may correspond to the docking device 1060 of FIG. 10A. When the indoor ultrasound diagnostic device 1061 corresponds to the docking device 1060, the indoor ultrasound diagnostic device 1061 may further include the display unit 1091 and the user interface unit 1092, unlike the docking device 1060. Furthermore, the processor 1075 of FIG. 10B may correspond to or include the pre-processor 1075 of FIG. 10A.

In addition, the second docking interface 1065, the second channel board 1070, the processor 1075, the control unit 1080, the display unit 1091, and the user interface unit 1092 of FIG. 10B may respectively correspond to the first docking interface 1040, the first channel board 1025, the image processing unit 1030, the control unit 1035, the display unit 1041, and the user interface unit 1045 described with reference to FIG. 10A and perform the same operations as those of their counterparts.

Only differences in configuration and operation of the indoor ultrasound diagnostic device 1061 from the docking device 1060 described with reference to FIG. 10A will now be described.

The second docking interface 1065 may include a wired communication interface (not shown) or a wireless communication interface (not shown) for performing wired or wireless communication with a first docking interface 1040 of a portable ultrasound diagnostic device 1020. Furthermore, the first docking interface 1040 may include a wired communication interface (not shown) or a wireless communication interface (not shown) for performing wired or wireless communication with the second docking interface 1065 of the indoor ultrasound diagnostic device 1061.

In this case, a wireless communication method may include at least one from among the above-described short-range data communication methods including WLAN, WI-FI, Bluetooth, Zigbee, WFD, IrDA, BLE, NFC, Wibro, WiMAX, SWAP, WiGig, and RF communication.

The second docking interface 1065 may transmit or receive data to or from the first docking interface 1040 of the portable ultrasound diagnostic device 1020. For example, the second docking interface 1065 may exchange at least one of an ultrasound signal, ultrasound data, and an ultrasound echo signal necessary for generating an ultrasound image with the first docking interface 1040.

Referring to FIG. 10B, the pre-processor 1075 may pre-process at least one ultrasound echo signal for which receive focusing has been performed by the second channel board 1070. In detail, the processor 1075 may adjust a gain of the at least one echo signal that has undergone the receive focusing in the second channel board 1070, perform filtering such as noise removal on the at least one echo signal, and perform digital signal processing for converting the at least one echo signal into a form suitable for transmitting it to the portable ultrasound diagnostic device 1020. Furthermore, when the portable ultrasound diagnostic device 1020 generates an ultrasound image, the at least one ultrasound echo signal subjected to pre-processing by the processor 1075 may be transmitted to the portable ultrasound diagnostic device 1020.

Furthermore, the processor 1075 may include an image processor (not shown). In this case, the processor 1075 may generate an ultrasound image by scan-converting pieces of ultrasound data received from the first and second channel boards 1025 and 1070 or pieces of ultrasound data received from the second channel board 1070. In detail, the processor 1075 may generate an ultrasound image by using at least one from among ultrasound echo signals generated by pre-processing pieces of ultrasound data received from the second channel board 1070 and ultrasound echo signals respectively corresponding to pieces of ultrasound data received from the first channel board 1025. In other words, in the embodiment shown in FIG. 10B, the processor 1075 may perform an operation of generating an ultrasound image, which is performed by the image processing unit 1030 of the portable ultrasound diagnostic device 1020.

In addition, an ultrasound image may include not only a grayscale ultrasound image obtained by scanning an object in an amplitude (A) mode, a brightness (B) mode, and a motion (M) mode, but also a Doppler image showing a moving object by using a Doppler effect. The Doppler image may include a blood flow Doppler image showing flow of blood (also referred to as a color Doppler image), a tissue Doppler image showing a movement of tissue, and a spectral Doppler image showing a moving speed of an object as a waveform.

Furthermore, the processor 1075 may generate a 3D ultrasound image by performing volume-rendering of volume data and generate an elasticity image by imaging deformation of an object due to a pressure. Furthermore, the processor 1075 may display various pieces of additional information in an ultrasound image by using texts and graphics. In addition, the generated ultrasound image may be stored in a memory (not shown) included in the indoor ultrasound diagnostic device 1061.

The control unit 1080 may control all operations of respective components of the indoor ultrasound diagnostic device 1061. In detail, the control unit 1080 may control a transmission beamforming operation and a reception beamforming operation of the second channel board 1070.

The power unit 1085 may supply power to respective components of the indoor ultrasound diagnostic device 1061. In detail, the power unit 1085 may include a power plug (not shown) for connecting with a wall power. The power unit 1085 may supply required power to the indoor ultrasound diagnostic device 1061 by using power received via the power plug.

The display unit 1091 displays a predetermined screen according to control by the control unit 1080. In detail, the display unit 1091 may include a display panel (not shown), and display a user interface screen, a medical image screen, etc. on the display panel. In detail, the display unit 1091 may display an ultrasound image generated by the processor 1075.

The user interface unit 1092 may create and output a user interface screen for receiving a predetermined command or data from a user. Furthermore, the user interface unit 1092 receives the predetermined command or the data from the user via the user interface screen. The user may recognize certain information by viewing the user interface screen displayed by the display unit 1091 and input a predetermined command or the data via the user interface unit 1092.

For example, the user interface unit 1092 may include a mouse, a keyboard, or another input device including hard keys for inputting predetermined data. For example, the user may manipulate at least one of the mouse, the keyboard, and the other input device included in the user interface unit 1092 to input predetermined data or the command.

As another example, the user interface unit 1092 may be formed as a touch pad. In detail, the user interface unit 1092 may include a touch pad (not shown) combined with the display panel included in the display unit 1091. In this case, the user interface screen is output onto the display panel. When a predetermined command is input via the user interface screen, the touch pad senses the command and transmits sensed information. Then, the control unit 1080 may analyze the sensed information to recognize and execute the command input by the user.

Furthermore, the display unit 1091 may display a menu screen for determining signals that are processed by the second channel board 1070 from among N number of signals for which transmission beamforming and reception beamforming are performed at one time. The user may set, via the user interface unit 1092, the signals that are processed by the second channel board 1070 from among the N number of signals. For example, the user may request processing by only the second channel board 1070 via the user interface unit 1092. As another example, the user may request, through the user interface unit 1092, the second channel board 1070 to process only signals corresponding to channels exceeding the number of channels that are to be processed by the first channel board 1025. Also, the user may individually set, via the user interface unit 1092, the number of channels processed by the first channel board 1025 and the number of channels processed by the second channel board 1070. Accordingly, the control unit 1080 may control the indoor ultrasound diagnostic device 1061 to perform operations corresponding to user requests.

Figure 11:
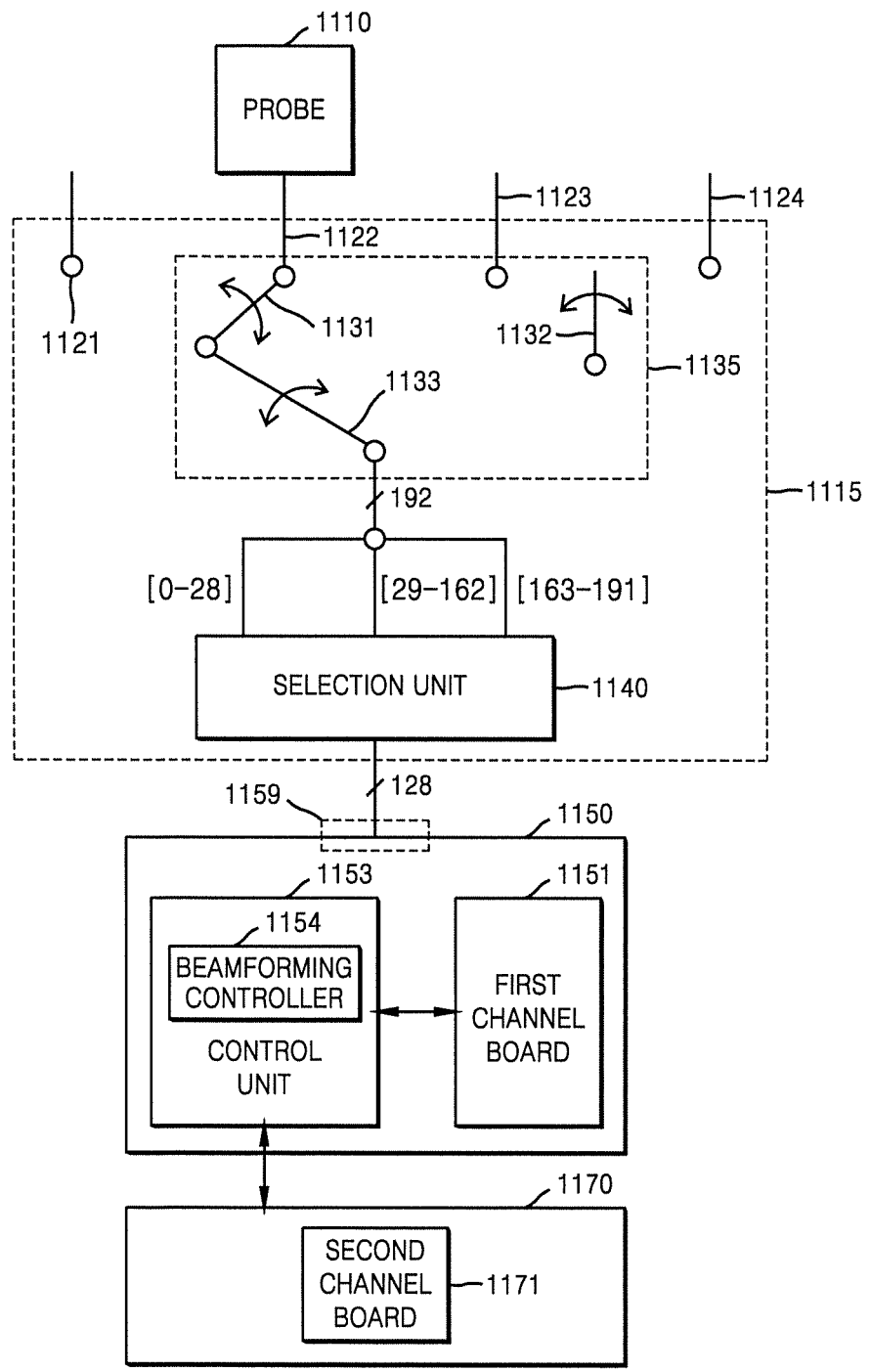
FIG. 11 is a block for describing, in detail, an ultrasound diagnostic system according to another embodiment of the present invention.

Referring to FIG. 11, a probe 1110, a PSA 1115, a portable ultrasound diagnostic device 1150, and a docking device 1170 respectively correspond to the probe 910, the PSA 915, the portable ultrasound diagnostic device 920, and the docking device 960 which have been described above with reference to FIG. 9. Therefore, a description repetitive of the descriptions of FIGS. 9 and 10 is not provided.

Referring to FIG. 11, the PSA 1115 may be provided at a probe connection terminal 1159 of the portable ultrasound diagnostic device 1150.

In detail, the PSA 1115 is an assemble for selecting a probe, and may include at least one or more probe connection ports 1121 to 1124, a probe selection switching unit 1135, and a selection unit 1140.

The same probe or different kinds of probes may be connected to the at least one or more probe connection ports 1121 to 1124. Here, the at least one or more probe connection ports 1121 to 1124 correspond to the at least one or more probe connection ports 321 to 325 of FIG. 3A.

When the probe 1110 is connected to the at least one or more probe connection ports 1121 to 1124, the probe selection switching unit 1135 senses the connection, and connects the selection unit 1140 to the probe connection port 1122 connected to the probe 1110. In detail, the probe selection switching unit 1135 includes at least one or more switches 1131 to 1133, and when the probe 1110 is connected to the at least one or more probe connection ports 1121 to 1124, as illustrated, the probe selection switching unit 1135 may turn on the switches 1131 and 1133 in order for the selection unit 1140 to be connected to the probe connection port 1122 connected to the probe 1110.

The selection unit 1140 transmits at least one of a plurality of signals, transmitted from the probe 1110, to the portable ultrasound diagnostic device 1150 at one time.

For example, the probe 1110 may be a 192-channel probe including 192 transducer elements. In this case, the probe 1110 generates ultrasound echo signals of 192 channels respectively received from the transducer elements of the 192 channels, and transmits the generated ultrasound echo signals corresponding to the 192 channels to the selection unit 1140 through the probe connection port 1122 and the probe selection switching unit 1135.

The selection unit 1140 may transmit 128 ultrasound echo signals, respectively corresponding to 128 channels among the received ultrasound echo signals of the 192 channels, to the portable ultrasound diagnostic device 1150 at one time. Also, the selection unit 1140 may subsequently transmit, to the portable ultrasound diagnostic device 1150, ultrasound echo signals of 64 channels except the ultrasound echo signals of the 128 channels among the ultrasound echo signals of the 192 channels.

In FIG. 11, a case in which the PSA 1115 transmits 128 signals, corresponding to the number of channels less than 192 that is the number of channels of the probe 1110, to the portable ultrasound diagnostic device 1150 at one time has been described above as an example, but as another example, the PSA 1115 may transmit signals, corresponding to 192 channels equal to the number of channels of the probe 1110, to the portable ultrasound diagnostic device 1150 at one time.

Moreover, the number of signals (the number of channels) which are transmitted to the portable ultrasound diagnostic device 1150 at one time may vary, or may vary depending on the product specification of the PSA 1115.

Figure 12:
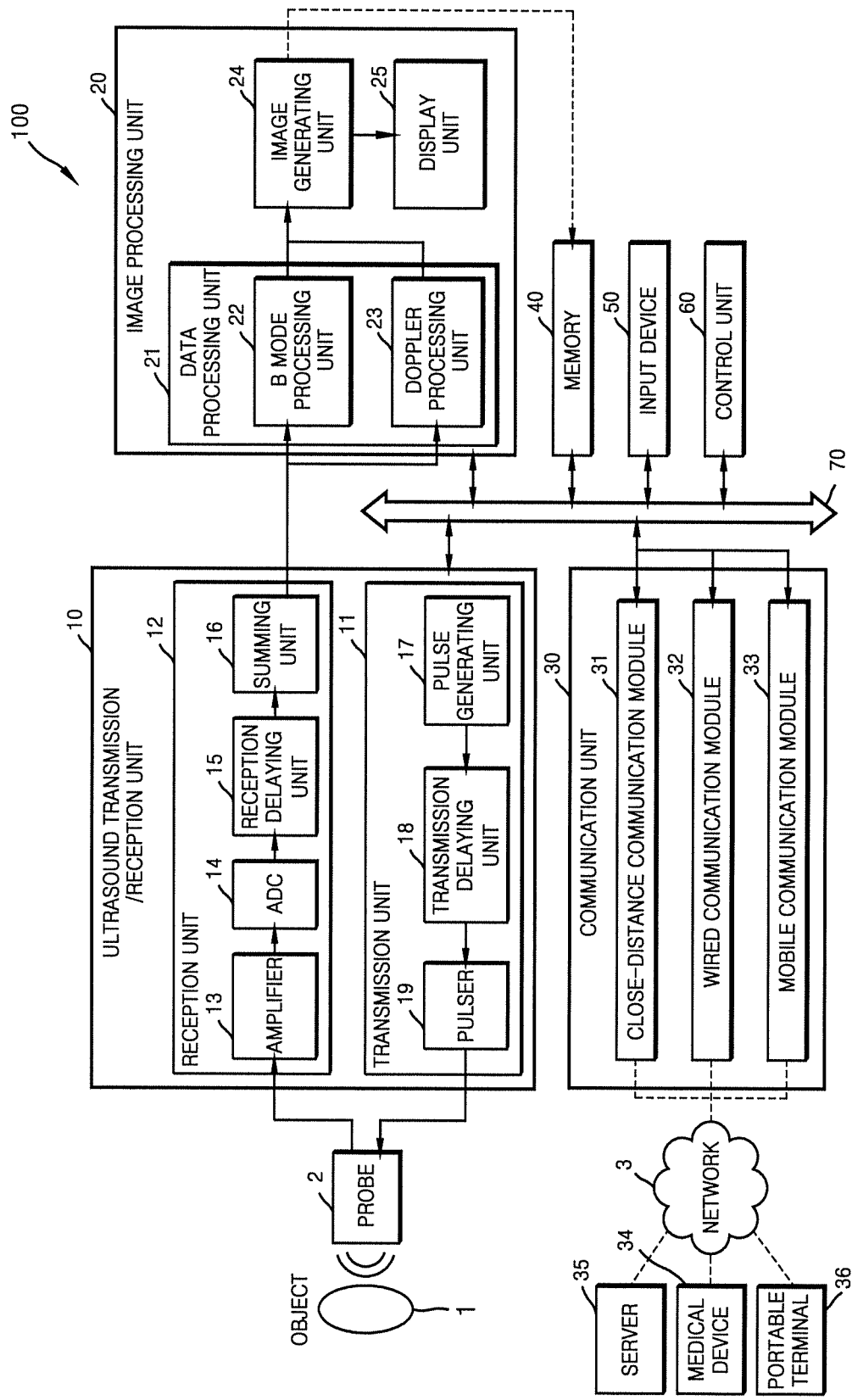
FIG. 12 is a diagram illustrating a portable ultrasound diagnostic device in detail.

FIG. 12 is a diagram illustrating a portable ultrasound diagnostic device in detail.

FIG. 12 is a diagram for describing in detail an ultrasound diagnostic system according to another embodiment of the present invention. In detail, the ultrasound diagnostic system 100 of FIG. 11 relates to a detailed configuration of the portable ultrasound diagnostic device 920 disclosed in an embodiment of the present invention. Thus, the operation and description of the portable ultrasound diagnostic device (e.g., the portable ultrasound diagnostic device 100, 200, 400, 920, or 1020) described above with reference to FIGS. 1 to 11 may be applied to a portable ultrasound diagnostic device 100 of FIG. 12 as-is. Furthermore, a probe 2 shown in FIG. 12 may correspond to the probe (e.g., the probe 101, 112, 114, 301, 910, or 1010) described with reference to FIGS. 1 through 11.

The portable ultrasound diagnosis device 100 may include the probe 2, an ultrasound transmission/reception unit 10, an image processing unit 20, a communication unit 30, a memory 40, an input device 50, and a control unit 60, where the components stated above may be connected to one another via buses 70.

The portable ultrasound diagnosis device 100 may be embodied not only as a cart type device, but also as a portable device. Examples of portable ultrasound diagnosis devices may include a PACS viewer, a smart phone, a laptop computer, a personal digital assistant (PDA), and a tablet PC. However, the present invention is not limited thereto.

The probe 2 transmits ultrasound waves to an object 1 based on a driving signal applied by the ultrasound transmission/reception unit 10 and receives echo signals reflected by the object 1. The probe 2 includes a plurality of transducers, and the plurality of transducers oscillate based on electric signals transmitted thereto and generate acoustic energy, that is, ultrasound waves. Furthermore, the probe 2 may be connected to the main body of the portable ultrasound diagnosis device 100 wiredly or wirelessly. According to embodiments of the present invention, the portable ultrasound diagnosis device 100 may include a plurality of probes 2.

A transmission unit 11 supplies a driving signal to the probe 2 and includes a pulse generating unit 17, a transmission delaying unit 18, and a pulser 19. The pulse generating unit 17 generates pulses for forming transmission ultrasound waves based on a predetermined pulse repetition frequency (PRF), and the transmission delaying unit 18 applies a delay time for determining transmission directionality to the pulses. Pulses to which a delay time is applied correspond to a plurality of piezoelectric vibrators included in the probe 2, respectively. The pulser 19 applies a driving signal (or a driving pulse) to the probe 2 as a timing corresponding to each pulse to which a delay time is applied.

A reception unit 12 generates ultrasound data by processing echo signals received from the probe 2 and may include an amplifier 13, an analog-digital converter (ADC) 14, a reception delaying unit 15, and a summing unit 16. The amplifier 13 amplifies echo signals in each channel, and the ADC 14 analog-digital converts the amplified echo signals. The reception delaying unit 15 applies delay times for determining reception directionality to the digital-converted echo signals, and the summing unit 16 generates ultrasound data by summing the echo signals processed by the reception delaying unit 15. Also, according to embodiments of the present invention, the reception unit 12 may not include the amplifier 13. In other words, if sensitivity of the probe 2 or the capability to process bit by the ADC 14 were enhanced, the amplifier 13 may be omitted.

The image processing unit 20 generates an ultrasound image by scan-converting ultrasound data generated by the ultrasound transmission/reception unit 10 and displays the ultrasound image. Meanwhile, an ultrasound image may include not only a grayscale ultrasound image obtained by scanning a target object in an amplitude (A) mode, a brightness (B) mode, and a motion (M) mode, but also a blood flow Doppler image showing flow of blood (aka a color Doppler image), a tissue Doppler image showing movement of tissues, and a spectral Doppler image showing moving speed of a target object as a waveform.

A B mode processing unit 22 extracts B mode components from ultrasound data and processes the B mode components. An image generating unit 24 may generate an ultrasound image indicating signal intensities as brightness based on the extracted B mode components.

Similarly, a Doppler processing unit 23 may extract Doppler components from ultrasound data, and the image generating unit 24 may generate a Doppler image indicating movement of a target object as colors or waveforms based on the extracted Doppler components.

The image generating unit 24 according to an embodiment of the present invention may generate a 3-dimensional (3D) ultrasound image via volume-rendering of volume data and may also generate an elasticity image which visualizes deformation of the object 1 due to a pressure. Furthermore, the image generating unit 24 may display various additional information in an ultrasound image by using texts and graphics. Meanwhile, the generated ultrasound image may be stored in the memory 40.

A display unit 25 displays the generated ultrasound image. The display unit 25 may display not only an ultrasound image, but also various information processed by the portable ultrasound diagnosis device 100 in a screen image via a graphic user interface (GUI). Meanwhile, the portable ultrasound diagnosis device 100 may include two or more display units 25 according to embodiments of the present invention.

The communication unit 30 is wiredly or wirelessly connected to a network 3 and communicates with an external device or a server. The communication unit 30 may exchange data with a hospital server or another medical device in a hospital that is connected with a picture archiving and communications system (PACS). Furthermore, the communication unit 30 may perform data communication according to the digital imaging and communications in medicine (DICOM) standard.

The communication unit 30 may transmit and receive data related to diagnosis of a target object, e.g., an ultrasound image, ultrasound data, and Doppler data of the target object, via the network 3 and may also transmit and receive medical images obtained via other medical devices, e.g., a CT image, a MR image, and an X-ray image. Furthermore, the communication unit 300 may receive information related to diagnosis history or treatment schedule of a patient from a server and utilizes the information for diagnosing the patient. Furthermore, the communication unit 30 may perform data communication not only with a server or a medical device in a hospital, but also with a portable terminal of a doctor or a patient.

The communication unit 30 is connected to the network 3 wiredly or wirelessly and may exchange data with a server 35, a medical device 34, or a portable terminal 36. The communication unit 30 may include one or more components that enable communication with external devices, e.g., a close-distance communication module 31, a wired communication module 32, and a mobile communication module 33. Furthermore, the medical device 34 may correspond to the docking device (e.g., the docking device 300, 960, or 1060) or the indoor ultrasound diagnostic device (e.g., the indoor ultrasound diagnostic device 500 or 1061) described with reference to FIGS. 1 through 11. In this case, the communication unit 30 may include the first docking interface (e.g., the first docking interface 940 or 1040) described above, and perform wired or wireless communication that is performed by the first docking interface (e.g., 940 or 1040).

The close-distance communication module 31 may refer to a module for close-distance communication within a predetermined distance. Examples of close-distance communication techniques according to an embodiment of the present invention may include wireless LAN, Wi-Fi, Bluetooth, Zigbee, Wi-Fi Direct (WFD), ultra wideband (UWB), infrared data association (IrDA), Bluetooth Low Energy (BLE), and near field communication (NFC). However, the present invention is not limited thereto.

The wired communication module 32 refers to a module for communication using electric signals or optical signals. Examples of wired communication techniques according to an embodiment of the present invention may include a pair cable, a coaxial cable, an optical fiber cable, and an Ethernet cable.

The mobile communication module 33 transmits and receives wireless signals with at least one from among a station, an external terminal, and a server on a mobile communication network. Here, the wireless signals may include voice call signals, video call signals, or various types of data for transmission and reception of text/multimedia messages.

The memory 40 stores various data processed by the portable ultrasound diagnosis device 100. For example, the memory 40 may store medical data related to diagnosis of a target object, such as ultrasound data and ultrasound image that are input or output and may also store algorithms or programs to be executed in the portable ultrasound diagnosis device 100.

The memory 40 may be embodied as any of various storage media, e.g., a flash memory, a hard disk drive, an EEPROM, etc. Furthermore, the portable ultrasound diagnosis device 100 may utilize a web storage or a cloud server that functions as the memory 40 online.

The input device 50 refers to a means via which a user inputs data for controlling the ultrasound diagnosis device 100. The input device 50 may include hardware components, such as a keypad, a mouse, a touch panel, a touch screen, and a jog switch. However, the present invention is not limited thereto, and the input device 50 may further include various other input means including an electrocardiogram measuring module, a respiration measuring module, a voice recognition sensor, a gesture recognition sensor, a fingerprint recognition sensor, an iris recognition sensor, a depth sensor, a distance sensor, etc.

The control unit 60 may control overall operations of the portable ultrasound diagnosis device 100. In other words, the control unit 60 may control operations among the probe 2, the ultrasound transmission/reception unit 10, the image processing unit 20, the communication unit 30, the memory 40, and the input device 50 shown in FIG. 12.

All or some of the probe 2, the ultrasound transmission/reception unit 10, the image processing unit 20, the communication unit 30, the memory 40, the input device 50, and the control unit 60 may be operated by software modules. However, the present invention is not limited thereto, and some of the components stated above may be operate by hardware modules. Furthermore, at least one of the ultrasound transmission/reception unit 10, the image processing unit 20, and the communication unit 30 may be included in the control unit 60. However, the present invention is not limited thereto.

Although a few embodiments of the present invention have been shown and described, it would be appreciated by those skilled in the art that changes may be made in these embodiments without departing from the principles and spirit of the invention, the scope of which is defined in the claims and their equivalents.

The invention claimed is:

1. An ultrasound diagnostic system, comprising:
a first ultrasound diagnostic device which is a portable device and including a first channel board comprising a first beamformer configured to perform beamforming of at least one of signals transmitted to or received from a plurality of transducer elements included in a probe; and
a second ultrasound diagnostic device configured to communicate with the first ultrasound diagnostic device and including a second channel board comprising a second beamformer configured to perform beamforming of at least one of the signals transmitted to or received from the plurality of transducer elements,
wherein a resolution, based on a maximum receivable number of signal channels for beamforming, is changeable by either using both the first and second channel boards or using the second channel board only,
wherein a number of signal channels, for which beamforming is performed by the second channel board, is greater than a number of signal channels for which beamforming is performed by the first channel board, and
wherein a total number of signal channels for beamforming is extended to a sum of the number of signal channels corresponding to the second channel board and the number of signal channels corresponding to the first channel board by using both the first and second channel boards.

2. The ultrasound diagnostic system of claim 1, wherein the first ultrasound diagnostic device further includes:
an image processing unit configured to:

receive at least one ultrasound echo signal received by the second channel board, and generate an ultrasound image by using a plurality of ultrasound echo signals including the at least one ultrasound echo signal received by the second channel board, and wherein a total number of the plurality of ultrasound echo signals used for generating the ultrasound image is more than ultrasound echo signals received and collected by the first channel board.

3. The ultrasound diagnostic system of claim 1, wherein the second ultrasound diagnostic device further includes:

an image processing unit configured to:

receive at least one ultrasound echo signal received by the first channel board, and generate an ultrasound image by using a plurality of ultrasound echo signals including the at least one ultrasound echo signal received by the first channel board and at least one ultrasound echo signal received by the second channel board, and wherein a total number of the plurality of ultrasound echo signals used for generating the ultrasound image is more than ultrasound echo signals received and collected by the first channel board.

4. The ultrasound diagnostic system of claim 1, further comprising the probe including the plurality of transducer elements and configured to communicate with the first ultrasound diagnostic device.

5. The ultrasound diagnostic system of claim 4, wherein the probe is further configured to transmit at least one of signals which is received from the plurality of transducer elements to the first ultrasound diagnostic device.

6. The ultrasound diagnostic system of claim 1, wherein the first ultrasound diagnostic device further comprises the probe.

7. The ultrasound diagnostic system of claim 1, wherein the first ultrasound diagnostic device further comprises a first docking interface unit including at least one of a wired communication interface and a wireless communication interface, wherein the second ultrasound diagnostic device further comprises a second docking interface unit including at least one of the wired communication interface and the wireless communication interface, and wherein the first ultrasound diagnostic device communicates with the second ultrasound diagnostic device by using the first docking interface unit, and the second ultrasound diagnostic device communicates with the first ultrasound diagnostic device by using the second docking interface unit.

8. The ultrasound diagnostic system of claim 1, wherein the wireless communication interface includes at least one communication module which performs wireless communication via at least one of Wireless LAN, Bluetooth, zigbee, WFD (Wi-Fi Direct), IrDA (infrared Data Association), BLE (Bluetooth Low Energy), NFC(Near Field Communication), Wibro (Wireless Broadband Internet), WiMAX (World Interoperability for Microwave Access), SWAP (Shared Wireless Access Protocol), WiGig (Wireless Gigabit Alliance) and RF communication.

9. The ultrasound diagnostic system of claim 1, wherein the second channel board performs beamforming of signals equal to a number of signals transmitted to or received from the probe.

10. The ultrasound diagnostic system of claim 1, wherein the probe transmits a plurality of ultrasound echo signals respectively corresponding to the plurality of transducer elements, the first channel board receives and collects at least one of the plurality of ultrasound echo signals transmitted from the probe, and the second channel board receives at least one ultrasound echo signal, corresponding to at least one channel, of the plurality of ultrasound echo signals transmitted from the probe, and collects the received at least one ultrasound echo signal.

11. The ultrasound diagnostic system of claim 2, wherein the image processing unit generates the ultrasound image by using at least one ultrasound echo signal selected from the at least one of the plurality of ultrasound echo signals received and collected by the first channel board and the at least one ultrasound echo signal transmitted from the second channel board.

* * * * *